(12) United States Patent
Vasin et al.

(10) Patent No.: US 6,920,348 B2
(45) Date of Patent: Jul. 19, 2005

(54) METHOD AND APPARATUS FOR DETERMINING METABOLIC FACTORS FROM AN ELECTROCARDIOGRAM

(75) Inventors: Eugene Vasin, Campbell, CA (US); Alexander Gelfenbain, Mountain View, CA (US)

(73) Assignee: Eugene V. Vasin, Campbell, CA (US)

( * ) Notice: Subject to any disclaimer, the term of this patent is extended or adjusted under 35 U.S.C. 154(b) by 181 days.

(21) Appl. No.: 10/364,647

(22) Filed: Jan. 31, 2003

(65) Prior Publication Data

US 2003/0171684 A1 Sep. 11, 2003

Related U.S. Application Data

(63) Continuation of application No. 09/921,662, filed on Aug. 3, 2001.

(51) Int. Cl.[7] ............................................. A61B 5/0402
(52) U.S. Cl. ....................................................... 600/509
(58) Field of Search ................................. 600/509–521

(56) References Cited

U.S. PATENT DOCUMENTS 5,810,722 A    9/1998 Heikkila ..................... 600/300
6,104,947 A    8/2000 Heikkila et al. ............ 600/519

FOREIGN PATENT DOCUMENTS

WO    WO 01/87139 A2    5/2001

OTHER PUBLICATIONS

U.S. Appl. No. 09/854,988, filed May 13, 2001, Masakov et al.

Dushanin S.A., et al., Kiev Sports Medicine University, 1986.

*Primary Examiner*—Scott M. Getzow

(57) ABSTRACT

Methods and devices are provided for determining metabolic factors using electrocardiogram measurements from a person's Wilson points. A first derivative of an electrocardiogram measurement is calculated. A ratio is calculated of the absolute value of the positive spike of the first derivative to the sum of the absolute values of the positive and negative spikes. In some embodiments, the ratio is multiplied by a constant to determine a metabolic factors. Further operations may be performed on the ratio to determine other metabolic factors. In some embodiments, a garment is provided for easily locating Wilson points. Methods and devices are provided for taking and processing EGC measurements to determine metabolic factors and for using the metabolic factors to optimize an exercise program.

21 Claims, 13 Drawing Sheets

METHOD AND APPARATUS FOR DETERMINING METABOLIC FACTORS FROM AN ELECTROCARDIOGRAM

REFERENCE TO RELATED APPLICATIONS

This application is a continuation of application Ser. No. 09/921,662 filed Aug. 3, 2001.

BACKGROUND OF THE INVENTION

This invention relates generally to the field of sports medicine. The invention relates more specifically to methods and devices for measuring metabolic factors relating to athletic performance and to designing training programs which account for such measurements.

The goal of athletic training is to attain an optimal athletic condition when an athlete is ready to compete without harming the athlete's body. Athletic training includes two major components. The first component involves training the required sports skills or technique. The second component involves training the power, stamina and the rate of muscular reactions. The second component usually includes three types of conditioning, applied at regular intervals: general physical conditioning; endurance training; and special training. General physical conditioning helps prepare an athlete for other types of training. Endurance training increases the metabolic capacity of an athlete. Special training concentrates on muscular activity specific for a chosen type of sport. Athletic training also causes activation of support systems—cardiovascular, respiratory, endocrine, excretory and nervous.

It is well known that certain metabolic factors are strongly indicative of an athlete's level of physical conditioning and potential for athletic performance. These metabolic factors are important for determining a person's level of athletic conditioning and for designing an optimal training schedule.

With slight variations, a cyclical training process is applicable to any kind of athletic activity. This process starts with a period of training aimed at gradually increasing an athlete's metabolic capacity, followed by an intensive period of training aimed at depleting the athlete's metabolic reserves.

Metabolic factors change over time and can be described in terms of temporal phases. When the athlete's metabolic factors reach maximum levels (during the "supercompensation phase"), the athlete achieves an optimal athletic condition and becomes ready to perform in a competition.

It is important to ensure that the supercompensation phase coincides with a competition in which the athlete will participate or the time of an intensive workout. Such timing requires a very experienced coach and a lack of physical and mental breakdowns on the part of the athlete. An experienced coach can subjectively estimate the phase of an athlete's metabolic factors based on the coach's intuition and feedback the coach receives from the athlete regarding the state of athlete's health. Traditional objective methods of monitoring metabolic factors, which include muscle biopsy, blood tests and gas-ergometry, are seldom used because they are cumbersome, time-consuming, traumatic to the athlete and expensive.

Due to the lack of suitable objective monitoring methods, athletes frequently over-exercise, resulting in "athletic overload syndrome" characterized by depression, atony, myocardiodystrophy, liver overtension syndrome and other symptoms. People who engage in physical activity for health reasons will also benefit from personalized training programs based on metabolic phases. Typically, they repeatedly engage in a similar physical activity of a submaximal intensity. Such activity enhances their general physical condition, but typically does not efficiently serve goals such as gaining muscle power, enhancing speed, losing weight or enhancing endurance.

Tying an exercise schedule to phases of metabolic factors would be a very efficient method for creating scientifically justified, efficient and personalized athletic training programs. However, in order to base an exercise schedule on phases of metabolic factors, one needs a fast, non-invasive and inexpensive method of determining metabolic factors.

SUMMARY OF THE INVENTION

Reliable methods and devices are disclosed for non-invasive determination of metabolic factors. According to one embodiment of the present invention, a method for determining a metabolic factor includes the steps of: obtaining a first derivative of an electrocardiogram measurement; determining $R_x$, an absolute value of a positive spike of the first derivative; determining $RS_x$, a sum of absolute values of the positive and negative spikes of the first derivative; and dividing $R_x$ by $RS_x$ to determine $V_x$, a number proportional to the metabolic factor.

According to another embodiment of the present invention, a method for determining a first metabolic factor includes the steps of: obtaining a first derivative of an electrocardiogram measurement of a V2 Wilson point; determining $R_2$, an absolute value of a positive spike of the first derivative of the electrocardiogram measurement of the V2 Wilson point; determining $RS_2$, a sum of absolute values of the positive and negative spikes of the first derivative of the electrocardiogram measurement of the V2 Wilson point; dividing $R_2$ by $RS_2$ to obtain $V_2$, a number proportional to a second metabolic factor; obtaining a first derivative of an electrocardiogram measurement of a V6 Wilson point; determining $R_6$, an absolute value of a positive spike of the first derivative of the electrocardiogram measurement of the V6 Wilson point; determining $RS_6$, a sum of absolute values of the positive and negative spikes of the first derivative of the electrocardiogram measurement of the V6 Wilson point; dividing $R_6$ by $RS_6$ to obtain $V_6$, a number proportional to a third metabolic factor; and performing an operation on $V_2$ and $V_6$ to determine the first metabolic factor.

According to another embodiment of the present invention, a method for determining a first metabolic factor includes the steps of: obtaining a first derivative of an electrocardiogram measurement of a V2 Wilson point; determining $R_2$, an absolute value of a positive spike of the first derivative of the electrocardiogram measurement of the V2 Wilson point; determining $RS_2$; a sum of absolute values of the positive and negative spikes of the first derivative of the electrocardiogram measurement of the V2 Wilson point; calculating $V_2$, a number proportional to a second metabolic factor; obtaining a first derivative of an electrocardiogram measurement of a V3R Wilson point; determining $R_{3R}$, an absolute value of a positive spike of the first derivative of the electrocardiogram measurement of the V3R Wilson point; determining $RS_{3R}$, a sum of absolute values of the positive and negative spikes of the first derivative of the electrocardiogram measurement of the V3R Wilson point; dividing $R_{3R}$ by $RS_{3R}$ to obtain $V_{3R}$, a number proportional to a third metabolic factor; obtaining a first derivative of an electrocardiogram measurement of a V6 Wilson point; determining $R_6$, an absolute value of a positive spike of the first derivative of the electrocardiogram measurement of the V6 Wilson point; determining $RS_6$, a sum of absolute values of the positive and negative spikes of the first derivative of the electrocardiogram measurement of the V6 Wilson point; dividing $R_6$ by $RS_6$ to determine $V_6$, a number proportional to a fourth metabolic factor; and performing an operation on $V_2$, $V_{3R}$ and $V_6$ to determine the first metabolic factor.

According to another embodiment of the present invention, a method of determining at least one metabolic factor of a person includes the steps of: securing a passive electrocardiogram positioning garment to the person, the passive electrocardiogram positioning garment accommodating a surface of the person's body and thereby orienting itself to locate a first Wilson point; attaching an electrode to the first Wilson point; measuring an electrocardiogram response at the first Wilson point; computing a first derivative of the electrocardiogram response; determining $R_x$, an absolute value of a positive spike of the first derivative; determining $RS_x$, a sum of absolute values of the positive and negative spikes of the first derivative; and dividing $R_x$ by $RS_x$ to determine $V_x$, a number proportional to the metabolic factor.

According to another embodiment of the present invention, a method of taking an electrocardiogram measurement includes the steps of: securing a passive electrocardiogram positioning garment to a person, the passive electrocardiogram positioning garment accommodating a surface of the person's body and thereby orienting itself to locate a first Wilson point; attaching an electrode to the first Wilson point; and measuring an electrocardiogram response at the first Wilson point.

According to another embodiment of the present invention, a method of taking an electrocardiogram measurement includes the steps of: donning a passive electrocardiogram positioning garment, the passive electrocardiogram positioning garment accommodating a surface of a person's body and thereby orienting itself to locate a position on the person's body; causing an electrode to be attached to the located position; and causing an electrocardiogram response to be measured at the located position.

According to another embodiment of the present invention, a garment for locating at least one Wilson point on a person's body includes: an illustration of at least one of the anatomical references used to locate a Wilson point; and an electrode positioning portion which indicates the position of the Wilson point.

According to another embodiment of the present invention, a device for passively locating at least one Wilson point of a person's body includes: a garment for accommodating a surface of the person's body and thereby orienting itself to the Wilson point; and an electrode positioning portion which is positioned by the garment at the person's Wilson point.

According to another embodiment of the present invention, an apparatus for determining metabolic factors from electrocardiogram measurements includes: means for obtaining a first derivative of an electrocardiogram measurement; means for determining $R_x$, an absolute value of a positive spike of the first derivative; means for determining $RS_x$, a sum of absolute values of the positive and negative spikes of the first derivative; and means for dividing $R_x$ by $RS_x$ to determine $V_x$, a number proportional to the metabolic factor.

According to another embodiment of the present invention, an apparatus for determining a first metabolic factor from electrocardiogram measurements includes: means for obtaining first derivatives of electrocardiogram measurements of a V2 Wilson point and a V6 Wilson point; means for determining $R_2$, an absolute value of a positive spike of the first derivative of the electrocardiogram measurement of the V2 Wilson point and for determining $R_6$, an absolute value of a positive spike of the first derivative of the electrocardiogram measurement of the V6 Wilson point; means for determining $RS_2$, a sum of absolute values of the positive and negative spikes of the first derivative of the electrocardiogram measurement of the V2 Wilson point and for determining $RS_6$, a sum of absolute values of the positive and negative spikes of the first derivative of the electrocardiogram measurement of the V6 Wilson point; means for dividing $R_2$ by $RS_2$ to obtain $V_2$, a number proportional to a second metabolic factor and for dividing $R_6$ by $RS_6$ to obtain $V_6$, a number proportional to a third metabolic factor; and means for performing an operation on $V_2$ and $V_6$ to determine the first metabolic factor.

According to another embodiment of the present invention, an apparatus for determining metabolic factors from electrocardiogram measurements includes: an input for receiving an electrocardiogram measurement; at least one processor for executing one or more software programs to process the electrocardiogram measurement to determine $R_x$ and $RS_x$, and to calculate $V_x$; and a memory for storing the software programs, wherein: $R_x$ is an absolute value of the positive spike of a first derivative of the electrocardiogram measurement; $RS_x$ is the sum of absolute values of the positive and negative spikes of the first derivative of the electrocardiogram measurement; and $V_x$ equals $R_x$ divided by $RS_x$.

According to another embodiment of the present invention, an apparatus for determining metabolic factors from electrocardiogram measurements includes: an input for receiving signals from an electrocardiogram unit; a processor for executing one or more software programs to determine $R_2$, $R_6$, $RS_2$ and $RS_6$, for calculating $V_2$ and $V_6$, and for performing an operation on $V_2$ and $V_6$ to determine the metabolic factor; and a memory for storing the software programs, wherein: $R_2$ is an absolute value of a positive spike of a first derivative of an electrocardiogram measurement of a V2 Wilson point; $RS_2$ is a sum of absolute values of the positive and negative spikes of the first derivative of the electrocardiogram measurement of the V2 Wilson point; $R_6$ is an absolute value of the positive spike of a first derivative of an electrocardiogram measurement of a V6 Wilson point; $RS_6$ is the sum of absolute values of the positive and negative spikes of the first derivative of the electrocardiogram measurement of the V6 Wilson point; $V_2$ equals $R_2$ divided by $RS_2$; and $V_6$ equals $R_6$ divided by $RS_6$.

According to another embodiment of the present invention, a storage medium stores software for controlling a computer to determine a metabolic factor from an electrocardiogram response by performing the steps of: obtaining a first derivative of an electrocardiogram measurement; determining $R_x$, an absolute value of a positive spike of the first derivative; determining $RS_x$, a sum of absolute values of the positive and negative spikes of the first derivative; and dividing $R_x$ by $RS_x$ to determine $V_x$, a number proportional to the metabolic factor.

According to another embodiment of the present invention, a storage medium stores software for controlling a computer to determine a metabolic factor from two electrocardiogram responses by performing the steps of: determining $R_2$, an absolute value of a positive spike of the first derivative of the electrocardiogram measurement of the V2 Wilson point; determining $RS_2$, a sum of absolute values of the positive and negative spikes of the first derivative of the electrocardiogram measurement of the V2 Wilson point;

dividing $R_2$ by $RS_2$ to obtain $V_2$, a number proportional to a second metabolic factor; obtaining a first derivative of an electrocardiogram measurement of a V6 Wilson point; determining $R_6$, an absolute value of a positive spike of the first derivative of the electrocardiogram measurement of the V6 Wilson point; determining $RS_6$, a sum of absolute values of the positive and negative spikes of the first derivative of the electrocardiogram measurement of the V6 Wilson point; dividing $R_6$ by $RS_6$ to obtain $V_6$, a number proportional to a third metabolic factor; and performing an operation on $V_2$ and $V_6$ to determine the first metabolic factor.

According to another embodiment of the present invention, a method of planning an exercise program includes the steps of determining a phase of a person's ECP factor based on an electrocardiogram measurement and recommending a workout according to the determined phase of the ECP factor.

According to another embodiment of the present invention, an apparatus for planning an exercise program includes means for determining a phase of a person's ECP factor based on an electrocardiogram measurement and means for recommending a workout according to the determined phase of the ECP factor.

According to another embodiment of the present invention, a method of planning an exercise program includes the steps of determining a phase of a person's ECP factor based on an electrocardiogram measurement and notifying the person of the phase of the ECP factor.

According to another embodiment of the present invention, an apparatus for planning an exercise program includes means for determining a phase of a person's ECP factor based on an electrocardiogram measurement and means for notifying the person of the phase of the ECP factor.

According to another embodiment of the present invention, a method for determining whether a child has the capability to become an outstanding athlete includes the steps of determining the child's energy conversion rate based on an electrocardiogram measurement and comparing the child's energy conversion rate to statistical information regarding the levels of energy conversion rate for children of a similar age.

According to another embodiment of the present invention, a method of determining whether a first athlete or a second athlete will engage in a competition includes the steps of: using a first electrocardiogram measurement to determine a first value of at least one of the first athlete's ECP factors; using a second electrocardiogram measurement to determine a second value of at least one of the second athlete's ECP factors; comparing the first value with the second value to determine whether the first athlete or the second athlete has the ECP factor with the higher value; and determining that the athlete whose ECP factor has the higher value will engage in the competition.

DESCRIPTION OF THE SPECIFIC EMBODIMENTS

Figure 1:
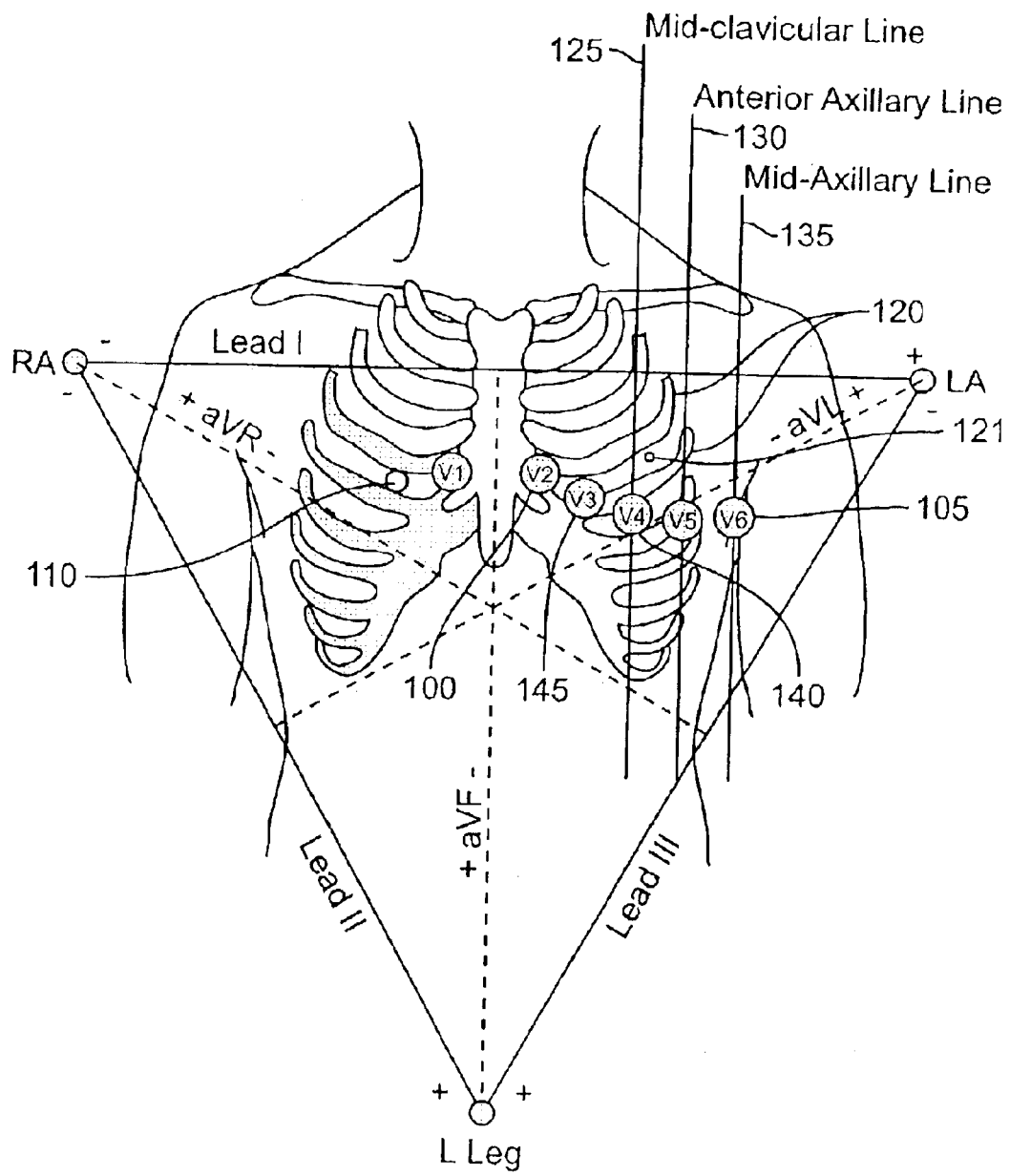
FIG. 1 indicates where the body's Wilson points are located.

Any muscular activity involves a complex group of biochemical reactions, which may be broadly characterized as energy metabolism, to take place in muscle tissue. These reactions are particularly significant in the myofibrils. During periods of muscular activity, energy is produced and utilized to cause a muscle to contract. Then, by-products of a biochemical reaction are released. Finally, a restitution process takes place that prepares the muscle for a further activity.

There are three main metabolic processes and three metabolites that can be utilized during the energy conversion processes which release energy for muscular contraction. They are characterized by numeric values which are referred to herein using various terms, including "metabolic factors," "factors of energy conversion processes" and "ECP factors." The duration and the level of intensity of a physical activity determine which of the three metabolites will be activated to supply energy to muscles. As noted in Table 1, below, energy conversion processes may be characterized by the level of lactic acid concentration in the blood.

TABLE 1

| Three primary metabolic processes | | |
| --- | --- | --- |
| Source of energy (metabolite) | Process | Level of lactic acid in blood |
| Phosphocreatine (creatine phosphate) | Anaerobic-alactic | none |
| Glucose (glycogen) | Mostly anaerobic-lactic | $\geq 4$ mMol/L |
| Carbohydrates, amino-acids and lipids | Mostly aerobic | $\leq 2$ mMol/L |

The anaerobic-alactic energy conversion process can last a very short time, typically up to 10 or 12 seconds. A physical activity that lasts longer than the anaerobic-alactic energy conversion process can support involves lactic acid accumulation in the blood. As the intensity of an exercise increases, lactic acid accumulates in the blood faster and the heart rate increases. As set forth in Table 2, the level of lactic acid concentration in the blood defines two important values, the aerobic threshold (AeT) and the anaerobic threshold (AnT). AeT and AnT have corresponding values of heart rates, which will be referred to herein as $HR_{AeT}$ and $HR_{AnT}$.

TABLE 2

Long duration energy conversion processes and related levels of lactic acid accumulation in blood

| Level of lactic acid concentration in the blood | Process |
|---|---|
| ≤2 mMol/L | Mostly aerobic |
| =2 mMol/L-Aerobic Threshold (AeT) | Mostly aerobic |
| 2–4 mMol/L | Aerobic-anaerobic |
| =4 mMol/L-Anaerobic Threshold (AnT) | Aerobic-anaerobic |
| ≥4 mMol/L | Mostly anaerobic-lactic |

Three numeric values—PhC, La, and $VO_2$ Max—characterize the three primary energy conversion processes. The anaerobic-lactic ECP factor (characterized by lactacidemia or La, the maximum attainable concentration of lactic acid in the blood) and the aerobic ECP factor ($VO_2$ Max, the maximal oxygen consumption level) describe the metabolic power and metabolic capacity of the corresponding energy conversion processes. The anaerobic-alactic ECP factor is characterized simply by the volume of its metabolite (phosphocreatine or PhC) available for release and utilization in working muscles.

The three primary metabolic processes involve different types of muscular activity, last for different periods of time and involve different chemical reactions. Some of these differences are summarized below in Table 3.

TABLE 3

Comparative chart of three energy conversion processes

| | Anaerobic-alactic | Anaerobic-lactic | Aerobic |
|---|---|---|---|
| Measurement | PhC—amount of phosphocreatine in muscles available for release and utilization during energy conversion process. It can be measured by invasive methods including muscular biopsy and creatine evaluation. | La (lactacidemia)— maximum attainable concentration of lactic acid in the blood. It can be measured by performing a blood test immediately (no delay whatsoever) upon completion of the specific physical activity. | $VO_2$ Max—maximal oxygen consumption level. It can be measured by analyzing exhaled gas mix collected during the peak of a specific muscular group workout. |
| Units | mg/g | $mMol*L^{-1}$ | $ml*min^{-1}*kg^{-1}$ |
| Muscular activity | Short duration, maximal intensity | Long duration, maximal intensity | Long duration, sub-maximal intensity |
| Typical duration of sustained energy production | 10–12 sec. | 20 sec.–30 min. | The time range is highly variable and is based on each person's level of fitness. |
| Typical physical activity | Spurts (sprint and weight lifting), team games that involve spurts (soccer, hockey), jumps | Short and medium distance running, high intensity sustained weight lifting, any physical activity which elevates the heart rate above $HR_{AeT}$ with incomplete restitution | Long distance running, cycling, cross-country skiing, etc. |
| Chemical reactions involved | Phosphocreatine stored in muscles breaks down, restoring ATP from AMP and producing creatine. During restitution, creatine is converted back to phosphocreatine. | Glucose stored in muscles as glycogen breaks down restoring ATP from AMP and producing lactic acid. | Carbohydrates, amino acids and lipids are broken down. ATP is restored from AMP and $CO_2$ and $H_2O$ are produced. |
| Restitution | Creatine is converted back to phosphocreatine. Oxygen is needed for this reaction. | Lactic acid needs to be broken down; this chemical reaction requires a lot of oxygen. | No restitution, but this energy conversion process is limited by the availability of metabolites and oxygen. |

TABLE 3-continued

Comparative chart of three energy conversion processes

|  | Anaerobic-alactic | Anaerobic-lactic | Aerobic |
|---|---|---|---|
| Heart rate | Unchanged during the physical activity, but elevated during recovery | Significantly elevated: can reach the maximal heart rate value | Elevated up to $HR_{AnT}$ |
| Respiration | Tensive apnea (cessation of breathing) during the physical activity, increases during recovery | Increased respiration rate, breathing through mouth only | Slightly increased respiration rate, breathing mostly through the nose |
| Blood pressure | Unchanged | Elevated | Decreased |

There are four zones of energy metabolism that are defined by the intensity of a physical workout, the energy source and the relationship to the aerobic threshold AeT and the anaerobic threshold AnT. These zones are set forth in Table 4, below. The ranges of heart rates are merely examples: in reality, individuals differ greatly with respect to $HR_{AeT}$ and $HR_{AnT}$.

TABLE 4

Zones of energy metabolism

| Zone | Metabolic Energy Source | Approximate Heart Rate | Relationship to AeT and AnT |
|---|---|---|---|
| I | Purely Aerobic | <140 | Below AeT |
| II | Aerobic/anaerobic | 140–160 | Between AeT and AnT |
| III | Anaerobic/lactic | <180 | Above AnT |
| IV | Anaerobic/restitution phase of phosphocreatinic | >180 | Above AnT |

Figure 7:
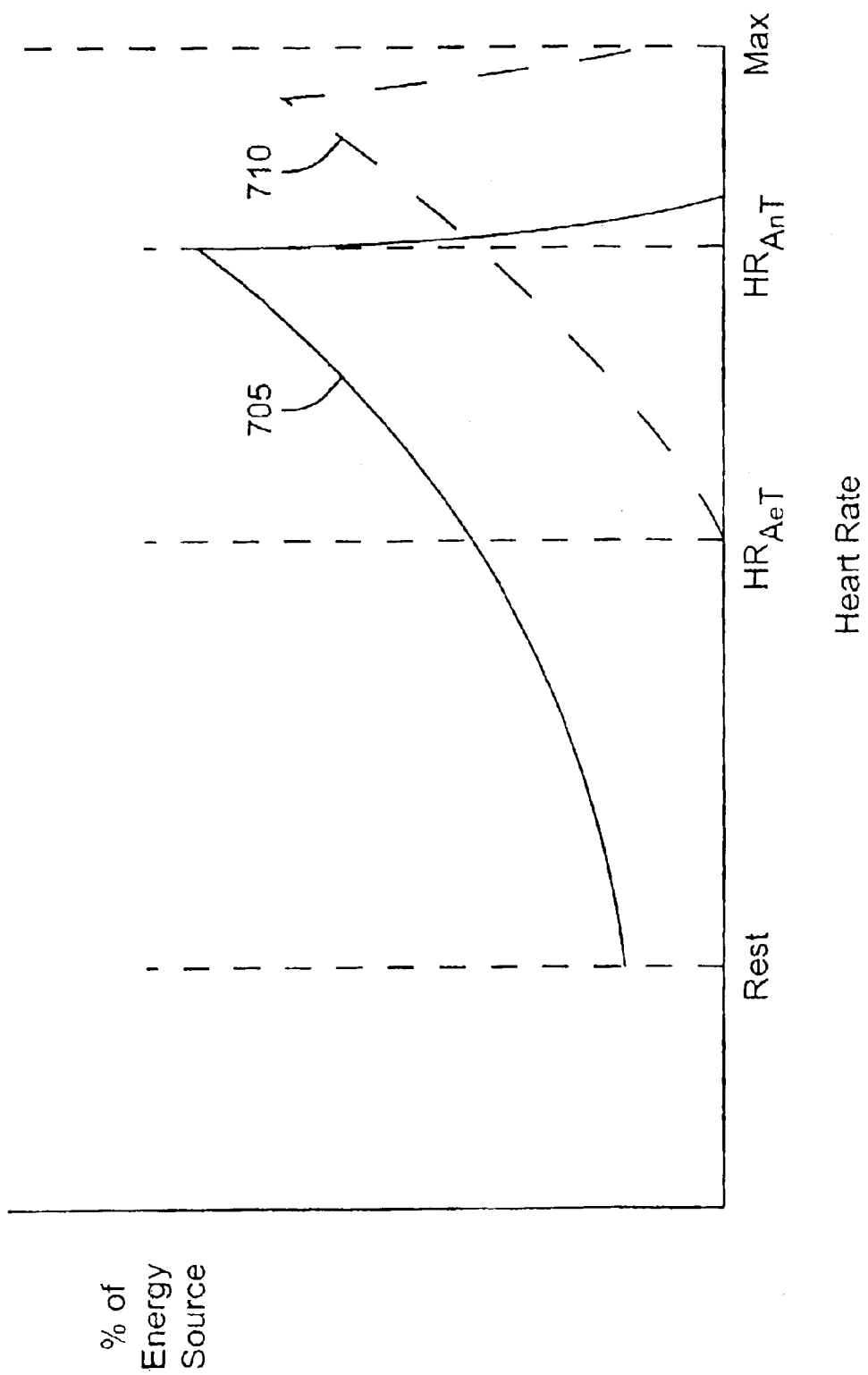
FIG. 7 is a graph which indicates the metabolic energy sources used at different heart rates.

These relationships are further illustrated in FIG. 7, wherein heart rate is depicted on the horizontal axis and the percent of energy source used is depicted on the vertical axis. Curve 705 represents a person's usage of aerobic energy sources (such as carbohydrates, amino acids and lipids) at varying heart rates. As shown by curve 705, a person's usage of aerobic energy sources increases to a maximum at or near $HR_{AnT}$, then steeply declines. Similarly, curve 710 indicates that a person's usage of anaerobic energy sources begins at $HR_{AeT}$, increases to a maximum value near the maximum heart rate, then steeply declines.

Two important attributes of an energy conversion process are metabolic power and metabolic capacity. The metabolic power of an energy conversion process is the rate of the biochemical reaction involved in the energy conversion process. Metabolic capacity is a characteristic of athletic performance that describes the volumes of metabolites available for energy conversion processes and the capacity of an athlete's body to perform the energy conversion process. This capacity depends on the state of cardiovascular, respiratory, endocrine, nervous and excretory systems.

Unpublished research by Dr. Vasin, based on studies of monozygotic and dizygotic twins, has indicated that the energy conversion rate is determined by heredity and can be measured starting at age 5 or 6. Systematic training can make the energy conversion rate grow by no more than approximately 15% from its base value. Energy conversion capacity, on the other hand, is more susceptible to systematic training and can be enhanced by approximately 40%.

Athletes of an Olympic-caliber have a very high energy conversion rate. The methods and devices of the present invention for determining human metabolic factors make it possible to predict with a high degree of certainty whether a child who has only begun training has the potential for a high level of achievement in competitive sports.

An important characteristic of a person's athletic condition is aerobic economy, which relates to the efficiency of the aerobic energy conversion process. The aerobic energy conversion process is the most economical of the three energy conversion processes since it does not require any restitution, can last the longest time and utilizes the least amount of metabolites. The greater the aerobic economy, the greater the intensity of the physical activity that the person is able to perform utilizing energy conversion processes which are available during aerobic activity. Aerobic economy is defined as a ratio of the intensity of muscular activity at AnT to the maximal intensity of a person's muscular activity. Average aerobic economy is 57–63%, while well-trained athletes have aerobic economy in the range of 70–74%.

A person's aerobic economy may be estimated from metabolic physical power at anaerobic threshold ($W_{AnT}$), $HR_{AeT}$ and $HR_{AnT}$. Two other indices, known as total metabolic capacity (TMC) and total anaerobic capacity (TAC), may be derived from the primary indices, $HR_{AnT}$ and/or $HR_{AeT}$. TMC indicates the total available energy, from all three metabolic sources, for a physical activity at near $VO_2$ Max level of intensity. TAC measures a person's availability of anaerobic metabolic sources to provide muscular work at a level of lactic and alactic metabolism. TAC relates to physical activity related to achieving maximal speed or maximal power.

Phases of ECP Factors

If one compiles a time series of a person's ECP factors, it can be observed that during periods when the person is not engaged in any significant physical activity on a regular basis, the values of the ECP factors do not change significantly (e.g., more than 25%) over time. These stable values are base values of the ECP factors for the person and the 25% range is the homeostasis zone for the value of each factor.

However, after an episode of an intensive specific physical activity (i.e., activity targeted primarily on a single energy conversion process), predictable changes in the corresponding ECP factor occur. These changes are summarized below in Table 5:

TABLE 5

Phases of ECP Factors

| Phase name | Description | Typical duration |
|---|---|---|
| 1 Decompensation | Starts during the episode of a physical activity. An ECP factor drops more than 25% from its base value | 30 min–6 hours |
| 2 Compensation | The ECP factor gets restored to its base value | PhC 2–48 hrs<br>La 2–120 hrs<br>VO$_2$ Max 3–10 days |
| 3 Supercompensation | If the person does not get engaged in a physical activity again, this phase starts after the compensation phase. The ECP factor may be more than 25% greater than its base value. | A couple of hours |
| 4 Subcompensation | The ECP factor drops again, but not very significantly | 1 hour–4 hours |
| 5 Stabilization | The ECP factor stabilizes at its new level, which may be 5–7% greater than its base value. | Lasts until the next workout or an episode of intensive physical activity |

Figure 8:
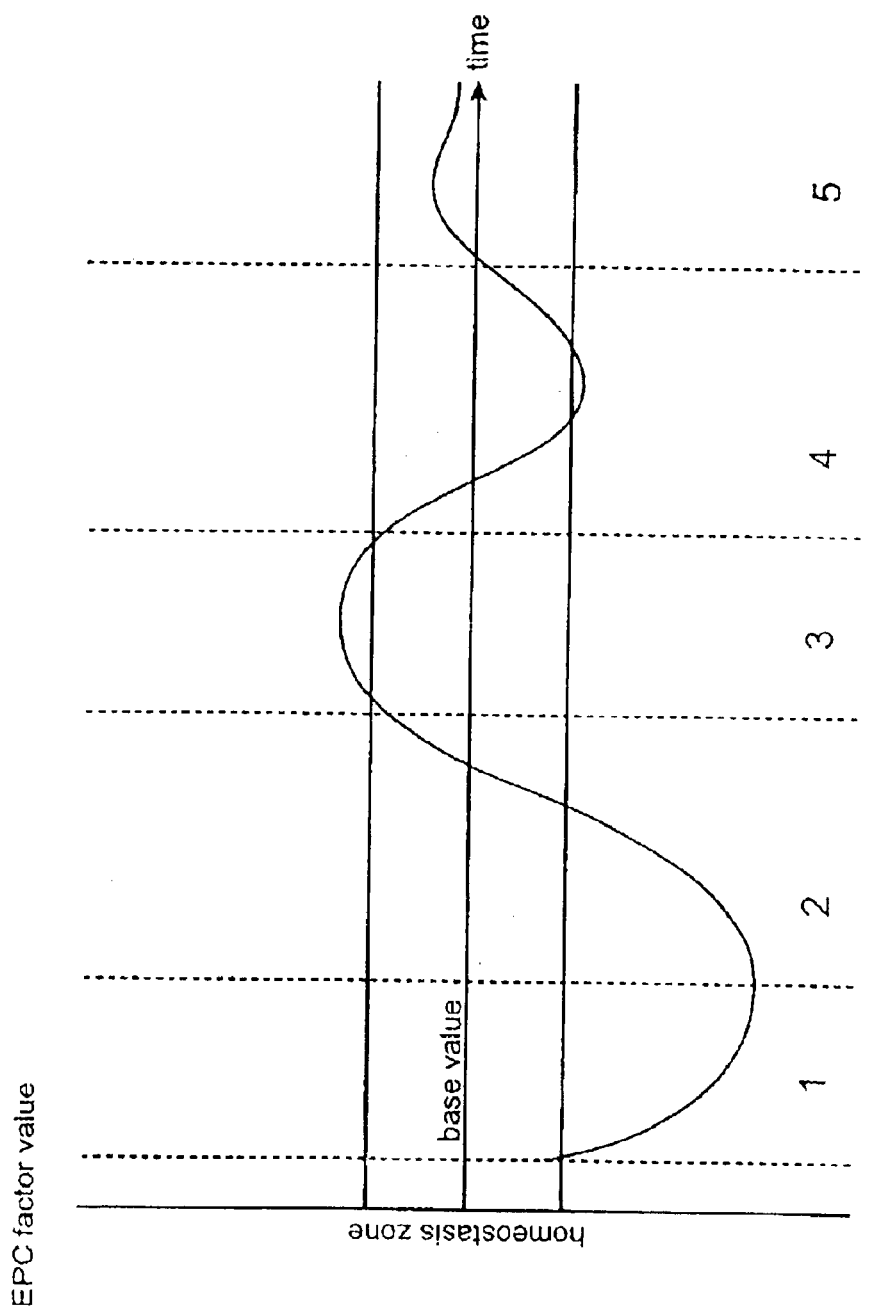
FIG. 8 is a graph which indicates the phases of metabolic indices after physical exercise.

The information in Table 5 is schematically depicted in FIG. 8.

Using ECP Factors in Creating Personalized Athletic Training Schedules

The best time for engaging in a competition or an episode of athletic training is the supercompensation phase of an appropriate ECP factor, because it is during this phase that the energy conversion process is in its most active state. The methods and devices of the present invention allow fast, non-invasive, and accurate measurement of ECP factors, therefore allowing the creation of accurate, personalized training schedules.

Moreover, the methods and devices allow a coach to quickly and reliably determine which of several possible competitors should be selected for a particular tournament, game or other competition: other factors being roughly equal, the coach may select the athlete with the highest ECP factors appropriate for the particular competition.

By synchronizing a training schedule with the supercompensation phases of ECP factors, athletes achieve significant increases in their performance without a risk of developing athletic overload syndrome. This synchronization also makes decompensation phases shorter in time, makes supercompensation phases greater in amplitude and makes the period between supercompensation phases smaller. A person is also be able to remain in good athletic shape by synchronizing the phases of the ECP factors.

There are two general kinds of athletic training episodes, intensive training and restitution workouts. The goal of the intensive training episode is the maximal load of one or more energy conversion systems. Intensive training is supposed to deplete an ECP factor (defined as difference in values of an ECP factor measured before and after the training episode) by 15–20% or more. The goal of the restitution workout episode is to recover from the previous episode of intensive training.

Since there are three different energy conversion processes, there are three different types of intensive training episodes, each characterized by the type and duration of exercises and restitution between them.

Intensive training for the anaerobic-alactic energy conversion process may be accomplished by performing short (e.g., 8–15 second) maximal intensity spurts (for example, running sprints or weight lifting) from a state of rest. Preferred embodiments of intensive training for the anaerobic-alactic energy conversion process include full restitution (heart rate approximately 15% below HR$_{AeT}$) between spurts. For example, a person first lifts the most weight that person can lift and performs between 1 and 3 repetitions. The person then waits until his or her heart rate drops to about 15% below HR$_{AeT}$ before the next brief episode of weight lifting. The process is then repeated.

Intensive training for the anaerobic-alactic energy conversion process may also be accomplished by lifting submaximal weight, but with the greatest number of repetitions a person can do during approximately 8–15 seconds. Generally speaking, either lifting maximal weight a moderate number of times or lifting moderate weight at a maximal speed (number of reps) should result in a maximal intensity exercise.

Intensive training for the anaerobic-lactic energy conversion process may be accomplished by performing longer (e.g., 20 second–3 min) maximal intensity exertions. Preferably, the same physical activity is used for anaerobic-alactic and anaerobic-lactic training. It is important to not achieve full restitution between the acceleration: the heart rate should not drop lower than the heart rate in the aerobic threshold—anaerobic threshold heart rate zone. For example, a person could begin jogging, then accelerate to a maximum speed for. 1 or 2 minutes, then jog during a partial restitution phase, then accelerate to a maximum speed for 1 or 2 minutes, and so on.

Intensive training for the aerobic energy conversion process is best performed by engaging in long duration cyclic physical activity (such as running, swimming or bicycling) while keeping the heart rate near the HR$_{AnT}$ value.

A restitution workout is performed with the heart rate in the HR$_{AeT}$–HR$_{AnT}$ range and it can involve any kind of physical activity. For example, such a workout could involve playing a sport.

More detailed examples of recommended exercise programs for various ECP phases will be discussed below.

Efficient Measurement of ECP Factors

The present invention includes methods and devices for the determination of the foregoing metabolic factors from electrocardiogram ("ECG") measurements of one or more Wilson points. FIG. 1 illustrates the locations of the body's Wilson points. The most significant Wilson points for the present invention are V2 (100), V6 (105) and V3R (110). As noted in FIG. 1, the Wilson points are located with reference to anatomical references such as ribs 120, intercostal spaces 121, mid-clavicular line 125, anterior axillary line 130 and mid-axillary line 135. V2 (100) is adjacent to the sternum in the left $4^{th}$ intercostal space. V4 (140) is at the intersection of the mid-clavicular line and the left $5^{th}$ intercostal space. V3 (145) is halfway between V2 (100) and V4 (140). V6 (105) is at approximately the same height as V4 (140) and on the mid-axillary line. V3R (110) is located in the same position as V3 (145), but on the right side of the body.

Figure 3:
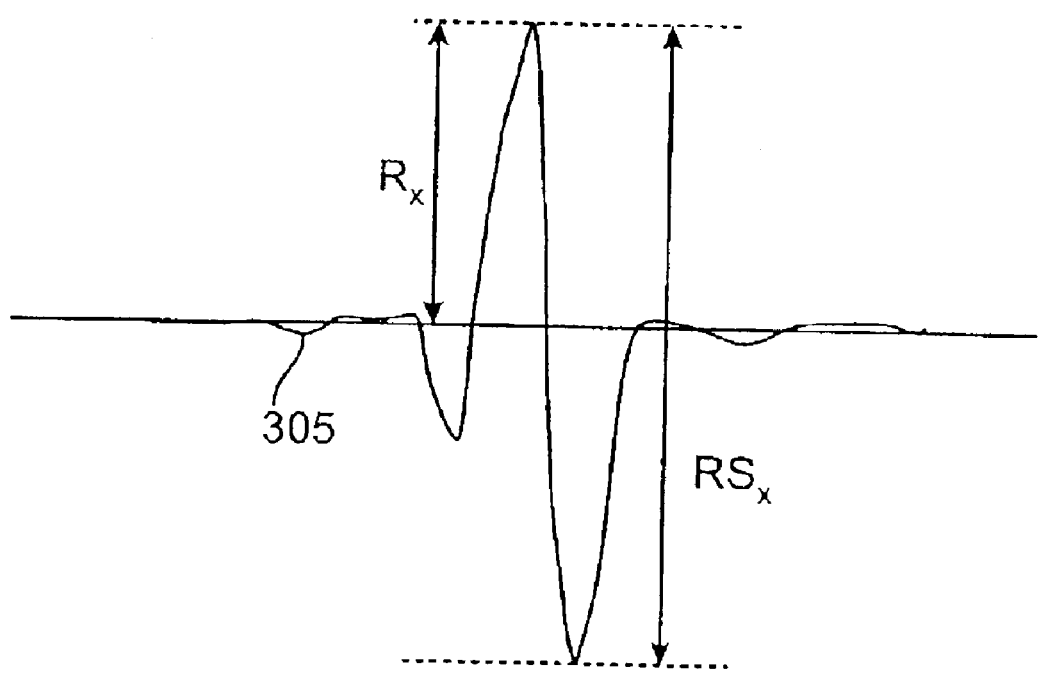
FIG. 3 illustrates a first derivative of an ECG signal.

The following formulas are based on absolute values of amplitude measurements of electrocardiogram signals. As shown in FIG. 3, $R_x$ denotes the absolute value of the R (positive) spike of a first derivative of electrocardiogram signal 305 measured at an arbitrary Wilson point Vx. $RS_x$ denotes the sum of absolute values of the R (positive) and S (negative) spikes of a first derivative of electrocardiogram signal 305 measured at Wilson point Vx.

The ratio of the absolute value $R_x$ to the value of $RS_x$ is specified as $V_x$:

$$V_x = R_x/RS_x \qquad \text{Equation (1)}$$

When in most formulae these ratios are specified as percentages, they are explicitly multiplied by 100. Often, only the changes in a person's metabolic factors will be of primary interest. It is important to understand that the following formulas are useful in computing relative values of the following metabolic factors, even if different constants are used. Only when the absolute values of metabolic factors are important, e.g., when comparing values from more than one person, is it necessary to use the constants which are disclosed in the formulas below.

It was demonstrated by statistical methods that the metabolic factors calculated according to the methods of the present invention correlate with metabolic factors measured by biochemical and other methods. The source ECG is taken when athletes are resting and not involved in any physical activity.

1. Aerobic Capacity: $VO_2$ Max $$VO_2 \text{ Max} = 1.2 V_6 * 100 [ml*min^{-1}*kg^{-1}] \qquad \text{Equation (2)}$$

$V_6$ is $V_x$ calculated (using Equation (1)) from the first derivative of an ECG signal measured at Wilson point V6, shown in FIG. 1. The accuracy of Equation (2) was statistically measured by comparing values produced by this formula and values determined by a gas analyzer. Samples were collected in plastic bags while oarsmen were rowing at their anaerobic threshold for 35 to 40 minutes and later analyzed with a Spirolit-2 device.

| Deviation | Match (% of data points) |
|---|---|
| ±10% | 97.5% |
| ±5% | 71.5% |

2. Anaerobic/Lactic Power and Capacity (Lactacidemia)

$$La = 0.3 V_2 * 100 [mMol*L^{-1}] \qquad \text{Equation (3)}$$

A comparison of La values calculated by Equation (3) and determined by invasive methods is set forth below:

| Deviation | Match (% of data points) |
|---|---|
| ±15% | 100% |
| ±10% | 91% |
| ±5% | 70% |

3. Anaerobic/Phosphocreatine Capacity (PhC)

$$PhC = 1.15 V_{3R} * 100 [mg*g^{-1}] \qquad \text{Equation (4)}$$

Olympic-level athletes have this index in the range of 50–60%.

There are significant difficulties of measuring phosphocreatine utilization by the muscle tissue for energy production. To prove the accuracy of Equation (4), values produced by it were compared with data measured by muscle biopsy prior to and after a 100 meter race. The correlation coefficient was 0.905.

Table 6, below, indicates a correlation in the range of 96% to 99% for data obtained using invasive testing with calculated values for the three metabolic indices discussed in the preceding section: $VO_2$ Max, La, and PhC. These measurements were performed in Moscow at Krylatskoye Stadium and in Sukhumi-Gali, Ga. at the Winter Olympic Camp. Invasive methods-biopsy, blood lactic acid test and specific ergospirometric testing-were performed by Professor Issurin's Research Group (Lezgoft Institute for Physical Culture and Sports Medicine, St. Petersburg). The athletes' names have been modified to protect their privacy.

TABLE 6

Comparison of Metabolic Factors Measured by Invasive Methods and by Calculation from ECG Measurements

| Athlete | Sex | $V_{3R}$ *100 | Biopsy | $V_2$ *100 | Lact (500 m) | $V_6$ *100 | $VO_2$ Max |
|---|---|---|---|---|---|---|---|
| Po | M | 80 | 68 | 59.4 | 20 | 76.4 | 76.4 |
| Da | M | 63.4 | 62.3 | 50.1 | 16.4 | 62.5 | 65 |
| Yur | M | 77.6 | 75.3 | 55.5 | 17.8 | 76.2 | 78.6 |
| Kor | M | 57.9 | 56.8 | 59.1 | 18.3 | 85.4 | 85.8 |
| Kon | M | 51.2 | 46.7 | 47.6 | 15.8 | 43.4 | 45.6 |
| Yav | M | 45 | 39.5 | 42.2 | 14 | 58.9 | 57.8 |
| Shap | M | 65.6 | 63.4 | 40 | 14 | 68.6 | 68.6 |
| Shap-ko | M | 52 | 57.1 | 57.1 | 18.9 | 88.9 | 88.8 |
| Parf | M | 48.9 | 47.6 | 46.4 | 15.5 | 68.4 | 69.2 |
| Mysg | M | 63.9 | 57.1 | 38.4 | 12.5 | 71.4 | 72 |
| Matuz | M | 23.8 | 18.9 | 25.6 | 7.9 | 65.9 | 65.9 |
| Bel | M | 51.7 | 52 | 33.3 | 12 | 59.2 | 56.2 |
| Anu | M | 42.7 | 46.9 | 26.6 | 8.8 | 57.1 | 57.4 |
| Sher | M | 31.3 | 32 | 26.8 | 9.1 | 50.4 | 48.9 |
| Pus | M | 47.8 | 55.2 | 19 | 6.5 | 54.2 | 54.8 |
| Lom | M | 25.5 | 18.9 | 38.3 | 13.1 | 51.9 | 56 |
| Shul | M | 75.4 | 73.3 | 40 | 13.7 | 57.6 | 63.5 |
| Vet | M | 46.7 | 44.3 | 46.1 | 14.9 | 81.6 | 83 |
| Nag | M | 88.4 | 83 | 31.1 | 10.2 | 56.5 | 57.2 |
| Log | M | 58.3 | 59.7 | 20.2 | 6.8 | 56.8 | 48.8 |
| Den | M | 37.7 | 37.4 | 30.3 | 10.3 | 54.9 | 54 |
| Kop | M | 63.1 | 63 | 45 | 15 | 62.4 | 63.1 |
| Trub | M | 42.9 | 38.2 | 36.5 | 12.5 | 55.4 | 53.9 |
| Gayd | M | 37.8 | 37.8 | 36.1 | 12.1 | 64.8 | 65.1 |
| Vod | M | 93 | 90.9 | 28.3 | 9 | 62.1 | 64.3 |
| Kis | M | 36.1 | 36 | 30 | 9.4 | 85.3 | 86 |
| Super | M | 65.2 | 65.3 | 34.6 | 11.1 | 78.4 | 77.9 |
| Kamal | M | 61.3 | 60 | 38.8 | 13.7 | 64.2 | 64.2 |
| Tsar | M | 56.8 | 57 | 43.3 | 14.2 | 52.9 | 54.7 |
| Kurl | M | 40.9 | 42.3 | 35.6 | 12 | 65.1 | 65.3 |
| Kalin | M | 34.7 | 34.7 | 27.4 | 9.1 | 46.1 | 48.8 |
| Smag | M | 32.3 | 32.2 | 18.5 | 6.7 | 72.1 | 72.9 |
| Zbyt | M | 76.3 | 76.3 | 43.4 | 15.1 | 64.8 | 66.1 |
| Tiker | M | 29.4 | 29.7 | 26 | 8.2 | 62.5 | 62.4 |

TABLE 6-continued

Comparison of Metabolic Factors Measured by Invasive Methods and by Calculation from ECG Measurements

| Athlete | Sex | $V_{3R}$ *100 | Biopsy | $V_2$ *100 | Lact (500 m) | $V_6$ *100 | $VO_2$ Max |
|---|---|---|---|---|---|---|---|
| Klem | M | 49.3 | 49.2 | 36.4 | 13 | 61.9 | 63.3 |
| Volk | M | 45.5 | 49.3 | 39 | 13.1 | 51.3 | 52.4 |
| Ren | M | 77.8 | 79 | 38.1 | 13.1 | 62.2 | 66 |
| Chern | M | 44.2 | 47.3 | 29.9 | 10.2 | 54.1 | 54.3 |
| Khokh | F | 64.5 | 65.3 | 38.1 | 13.3 | 60 | 62.1 |
| Nar | F | 67.5 | 48.7 | 60 | 20.3 | 66.7 | 64.2 |
| Lih | F | 35 | 35.3 | 27.2 | 9.1 | 60.5 | 58.8 |
| Simon | F | 34 | 35.6 | 32.1 | 11.2 | 49.4 | 50.2 |
| Izyum | F | 38.3 | 39 | 31.1 | 10.2 | 67.3 | 65.7 |
| Lev | F | 44.3 | 49.1 | 43.8 | 14.2 | 55.3 | 50.9 |
| Sharaf | F | 49.2 | 50.4 | 46.7 | 16 | 49.2 | 50.1 |
| Gut | F | 28.3 | 25 | 39.1 | 12.7 | 60.2 | 59.7 |
| Slap | F | 46.7 | 39.2 | 36.5 | 13.6 | 76.1 | 77.2 |
| Nikit | F | 82.1 | 82.7 | 54.3 | 18.1 | 58.8 | 57.3 |
| Chisl | F | 50 | 54.3 | 33.3 | 11 | 68.9 | 67.3 |
| Myzg | F | 92.3 | 87.3 | 41.8 | 12.8 | 57.9 | 58.2 |
| Sum | | 2647.6 | 2595.5 | 1904.1 | 636.5 | 3142.1 | 3155.9 |
| Mean | | 51.92 | 51.4 | 37.34 | 12.48 | 61.61 | 61.95 |
| Sigma | | | | | | | |
| Correlation | | 0.969515 | | 0.989023 | | 0.978733 | |

4. Aerobic Economy ($W_{AnT}$, $HR_{AeT}$ and $HR_{AnT}$)

Aerobic economy can be estimated from three indices: $W_{AnT}$, which is metabolic power at the anaerobic threshold; $HR_{AeT}$, which is heart rate at the aerobic threshold; and $HR_{AnT}$, which is heart rate at the anaerobic threshold. These indices may be determined from $V_6$ and $V_2$, as noted below:

$$W_{AnT}=(V_6*100)/(V_6+V_2) \text{ [\% of } VO_2 \text{ Max]} \quad \text{Equation (5)}$$

$$HR_{AnT}=V_6+V_2+W_{AnT}[\text{min}^{-1}] \quad \text{Equation (6)}$$

$$HR_{AeT}=(V_6*W_{AnT})/100+V_2+W_{AnT}[\text{min}^{-1}] \quad \text{Equation (7)}$$

The accuracy of Equations (5), (6) and (7) was measured by comparing these values with values measured by gas ergometry (using an exhaled gas mix collected during a specific workout) and by blood lactic acid testing.

| Deviation | Match |
|---|---|
| ±10% | 89.7% |
| ±5% | 76.7% |

5. Total Metabolic Capacity (TMC)

TMC indicates total available energy (considering all three metabolic sources) for a physical activity performed at near $VO_2$ Max level of intensity. It is measured in kilocalories (kCal).

$$TMC=V_6+V_2+V_{3R}+W_{AT}[\text{kCal}] \quad \text{Equation (8)}$$

6. Total Anaerobic Capacity (TAC)

Total anaerobic capacity measures the availability of anaerobic metabolic sources to provide muscular work at a level of lactic and alactic metabolism. This index reflects physical activity related to achieving maximum speed or maximum power.

$$TAC=100V_{3R}/(V_{3R}+V_2)+V_6+V_2+V_{3R}[\text{Cal}*\text{kg}^{-1}] \quad \text{Equation (9)}$$

Figure 2:
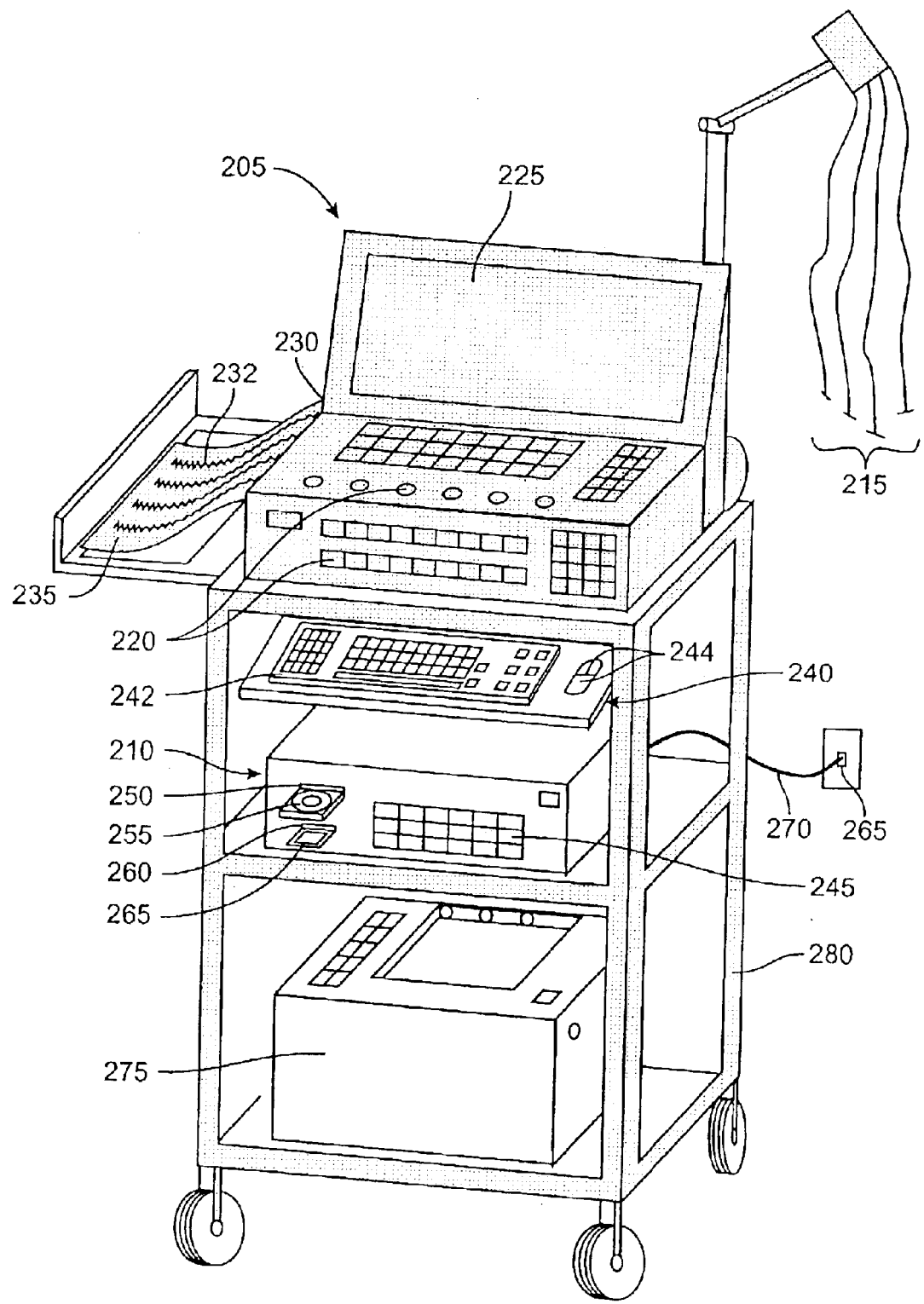
FIG. 2 illustrates an apparatus according to one embodiment of the present invention.

FIG. 2 illustrates an embodiment of an apparatus for taking electrocardiogram measurements, for determining metabolic factors from the electrocardiogram measurements and for designing an exercise program. The principal components of apparatus of FIG. 2 include ECG 205 and computer 210, which may be used separately or as a unit. In other embodiments, ECG 205 includes the software, memory and processor(s) necessary for performing the functions of computer 210.

In this embodiment, ECG 205 includes electrode leads 215 for receiving electrocardiogram signals 217 (not shown) from a person's heart. In the embodiments described in this disclosure, the signals are received from Wilson points, principally Wilson points $V_2$, $V_{3R}$ and $V_6$. However, ECG 205 may be used for other types of testing, such as conventional stress testing. In other embodiments, ECG 205 includes a wireless receiver for receiving signals transmitted from electrodes over a wireless link.

ECG 205 includes controls 220 necessary for specifying the normal functions of an ECG, such as what type of input is being received and what type of output is desired. In one embodiment, a user may control ECG 205 by interacting with a graphical user interface shown on display 225 via controls 220.

In the embodiment shown in FIG. 2, ECG 205 includes printer 230 for producing hard copies 232. Such hard copies may include individual ECG traces 235, interpretive text, etc.

Computer 210 preferably includes one or more input devices 240, such as keyboard 242, mouse 244 and controls 245, for receiving instructions from a user. In the embodiment shown in FIG. 2, display 225 is used by both ECG 205 and computer 210: a user may operate both ECG 205 and computer 210 by interacting with a graphical user interface which appears on display 225. In other embodiments, computer 210 has its own display.

In the embodiment shown in FIG. 2, computer 210 includes optical disk drive 250, floppy disk drive 260 and hard drive 252 (not shown). Preferably, optical disk drive 250 includes both data reading and data writing capabilities.

Computer 210 may be used as a "stand-alone" computer and may also be networked with other computers. As shown in FIG. 2, computer 210 and/or ECG 205 may be connected to the telephone network, to other computers in a local area network, a wide-area network, the Internet or other networks via communications port 265 and communications link 270. These connections allow updated software to be downloaded by computer 210, allow computer 210 to access data stored in other computers and provide other well-known advantages of networking with other computers via the Internet and otherwise. These connections also allow computer 210 or ECG 205 to send information to a user, e.g., regarding a time when one or more of the user's ECP factors may be in the supercompensation phase, regarding a recommended workout, etc.

In some embodiments, communications port 265 and communications link 270 allow a user to send ECG data to computer 210 and/or ECG 205 from another location. Wherever the ECG data originate, computer 210 and/or ECG 205 can process these data, determine ECP factors and notify the user regarding the values of the ECP factors, the phase of the ECP factors, recommended times, styles and intensities of workouts, etc.

In some embodiments, computer 210 and/or ECG 205 are networked to a database which includes data regarding a person's workouts. Such data may be obtained, for example, by one or more weight training machines, treadmills, cycles, rowing machines, cross-country skiing simulators or other equipment which the person uses for exercising. Such data may include the dates on which the person exercised, the amount of weight lifted by the person, the number of repetitions, the number of sets, the length of time of the exercise, estimated calories used (or other measurements of workout intensity), etc. In some embodiments, computer 210 and/or ECG 205 notify the user about the values of the ECP factors, the phase of the ECP factors, recommended times, styles and intensities of workouts, etc., via a display associated with the exercise equipment. In some such embodiments, the notifications include a recommended use of the particular equipment, such as the amount of weight, the number of repetitions in a set, the number of sets, the length and/or intensity of the workout, etc.

The apparatus shown in FIG. 2 includes printer 275 for output of hard copies from computer 210. In some embodiments, printer 275 is also used for output of data from ECG 205. However, it is advantageous to have a separate printer (such as printer 230) for output of ECG data, because of the special paper normally used for displaying these data.

Cart 280 provides a convenient movable structure for ECG 205, computer 210 and peripheral devices.

Normally, electrocardiogram signals 217 are in analog format. If this is the case, electrocardiogram signals 217 must be digitized by A/D converter 238 (not shown) in order to be processed using a digital computer. AID converter 238 may be a component of either ECG 205 or computer 210, or may be a stand-alone device. In the embodiment shown in FIG. 2, A/D converter 238 is a component of computer 210. Electrocardiogram signals 217 are transmitted from ECG 205 to computer 210 in analog form and are digitized by A/D converter 238 before being processed further.

All embodiments of the present invention require that a first derivative must be calculated for electrocardiogram signals 217. In the embodiment shown in FIG. 2A, processor 285 calculates a first derivative of electrocardiogram signals 217 after electrocardiogram signals 217 have been digitized. In other embodiments, a first derivative of electrocardiogram signals 217 is calculated before electrocardiogram signals 217 have been digitized. In one such embodiment, electrocardiogram signals 217 are input to an operational amplifier in analog form and the operational amplifier outputs a first derivative, which is then input to A/D converter 238.

Figure 2A:
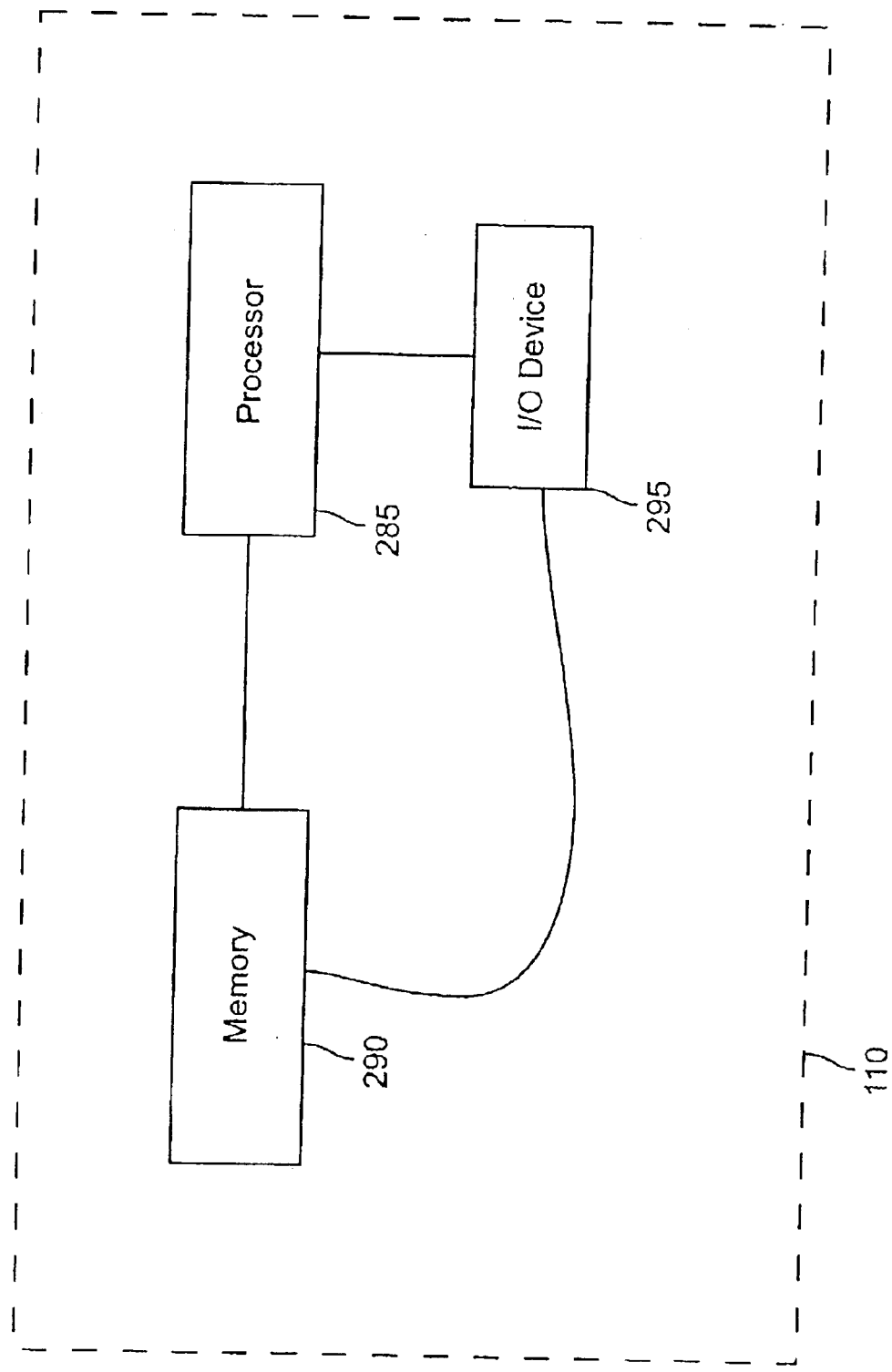
FIG. 2A illustrates components of computer 110 which are not visible in FIG. 2.

In the embodiment shown in FIG. 2A, processor 285 performs various calculations based upon software stored in memory 290. These calculations include the computation of various metabolic factors, the determination of their phases and matching the results with recommended workouts. In some embodiments, software is stored in processor 285 itself. Memory 290 is a representation of any convenient memory accessible to processor 285, including hard drive 252, solid state memory, optical disk 255 and floppy disk 265.

In some embodiments, processor 285 executes remote procedure calls received through I/O device 295 from another computer. In one such embodiment, remote procedure calls are received from the Internet via communications port 265 and communications link 270.

Procedures for Determining ECP Factors and Corresponding Recommended Exercise Programs Following are descriptions of some operations which are performed on electrocardiogram signals 217 in order to determine metabolic factors. As noted above, in the embodiment shown in FIGS. 2 and 2A these operations are performed by one or more processors of computer 210, such as processor 285. However, in other embodiments, processors located in other devices (such as ECG 205) perform these operations.

Figure 4:
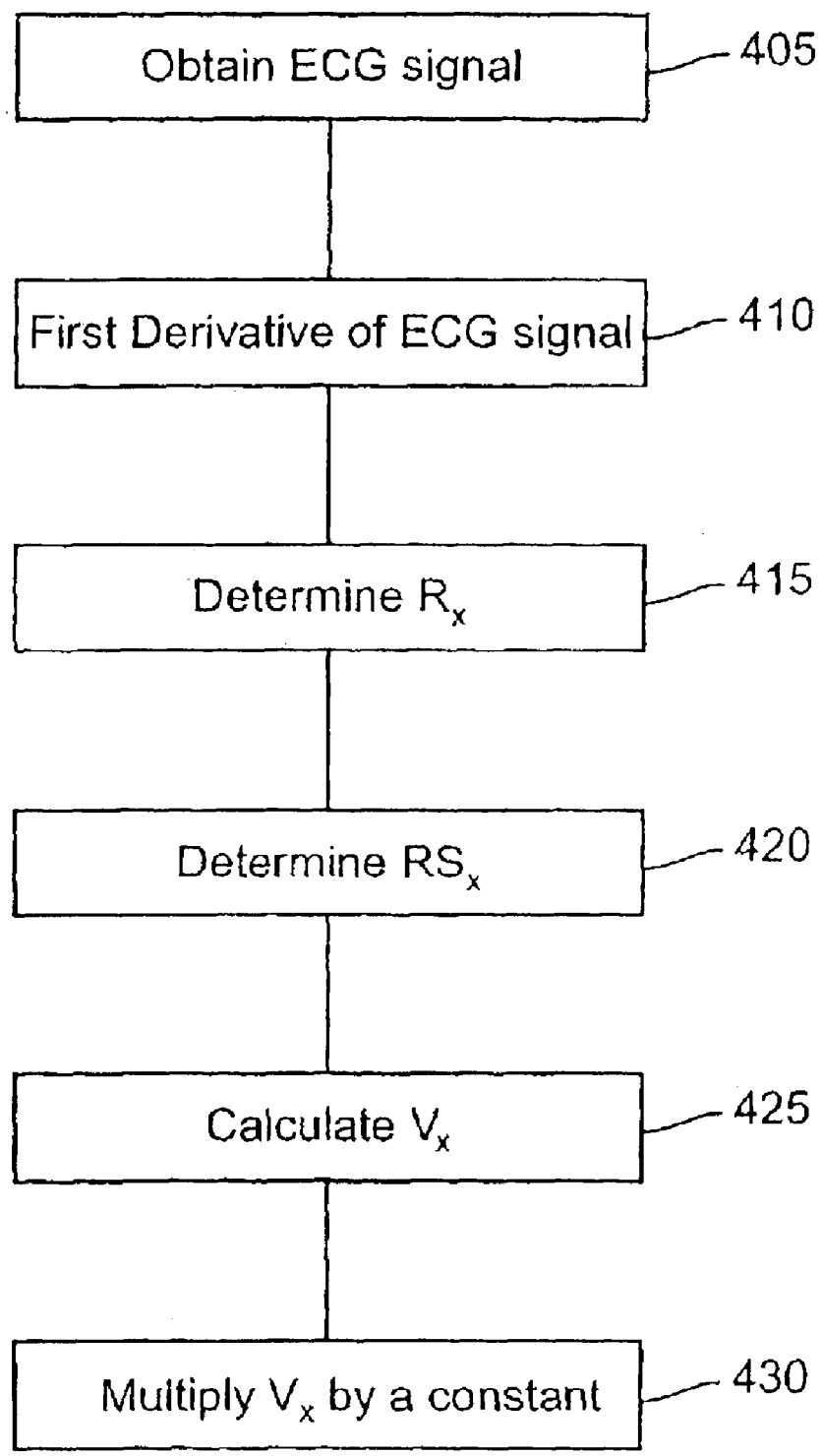
FIG. 4 is a flow chart which illustrates a method of determining a metabolic factor according to an embodiment of the present invention.

FIG. 4 is a flow chart which illustrates the process of calculating the primary ECP factors. In step 405, an ECG signal is obtained. The signal could be obtained, for example, via ECG 205, via a wireless link or over communications link 270. In step 410, the first derivative of the ECG signal is obtained. The first derivative could be calculated, for example, by processor 285, or could be output from a circuit such as an operational amplifier. In step 415, $R_x$ is determined. As noted above with reference to FIG. 3, $R_x$ denotes the absolute value of the R (positive) spike of a first derivative of electrocardiogram signal 305 measured at an arbitrary Wilson point $V_x$. In step 420, $RS_x$ is obtained. $RS_x$ denotes the sum of absolute values of the R (positive) and S (negative) spikes of a first derivative of electrocardiogram signal 305 measured at Wilson point VX.

Although in FIG. 4 (and other flow charts of this disclosure) the step of determining $R_x$ precedes the step of determining $RS_x$, in practice this need not be the case.

In step 425, $V_x$ (a number proportional to a primary ECP factor) is obtained by dividing $R_x$ by RSx. In optional step 430, $V_x$ is multiplied by a constant to determine a primary ECP factor.

Figure 5:
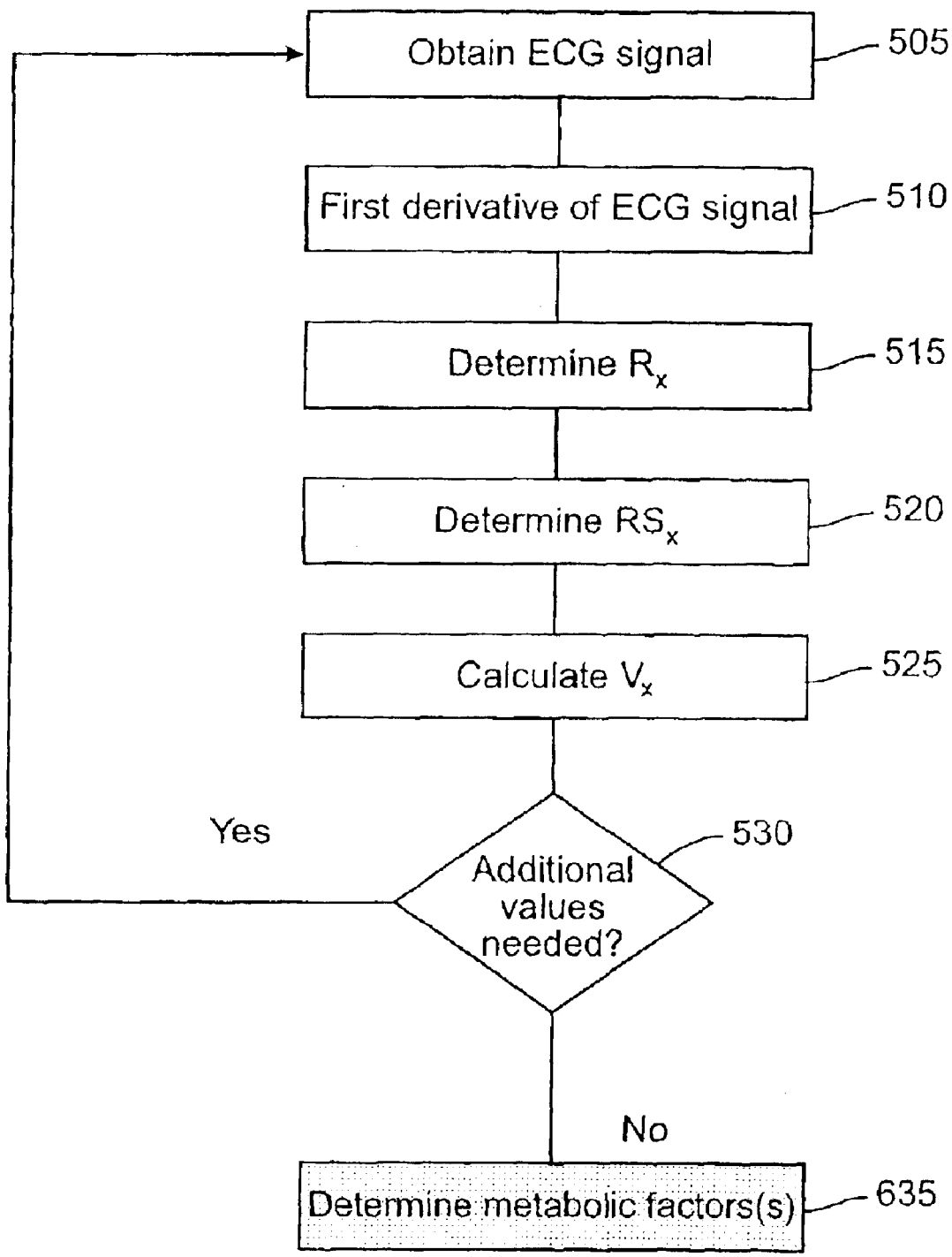
FIG. 5 is a flow chart which illustrates a method of determining a metabolic factor according to an embodiment of the present invention, wherein more than 1 value of $V_x$ is needed to compute the metabolic factor.
Figure 6:
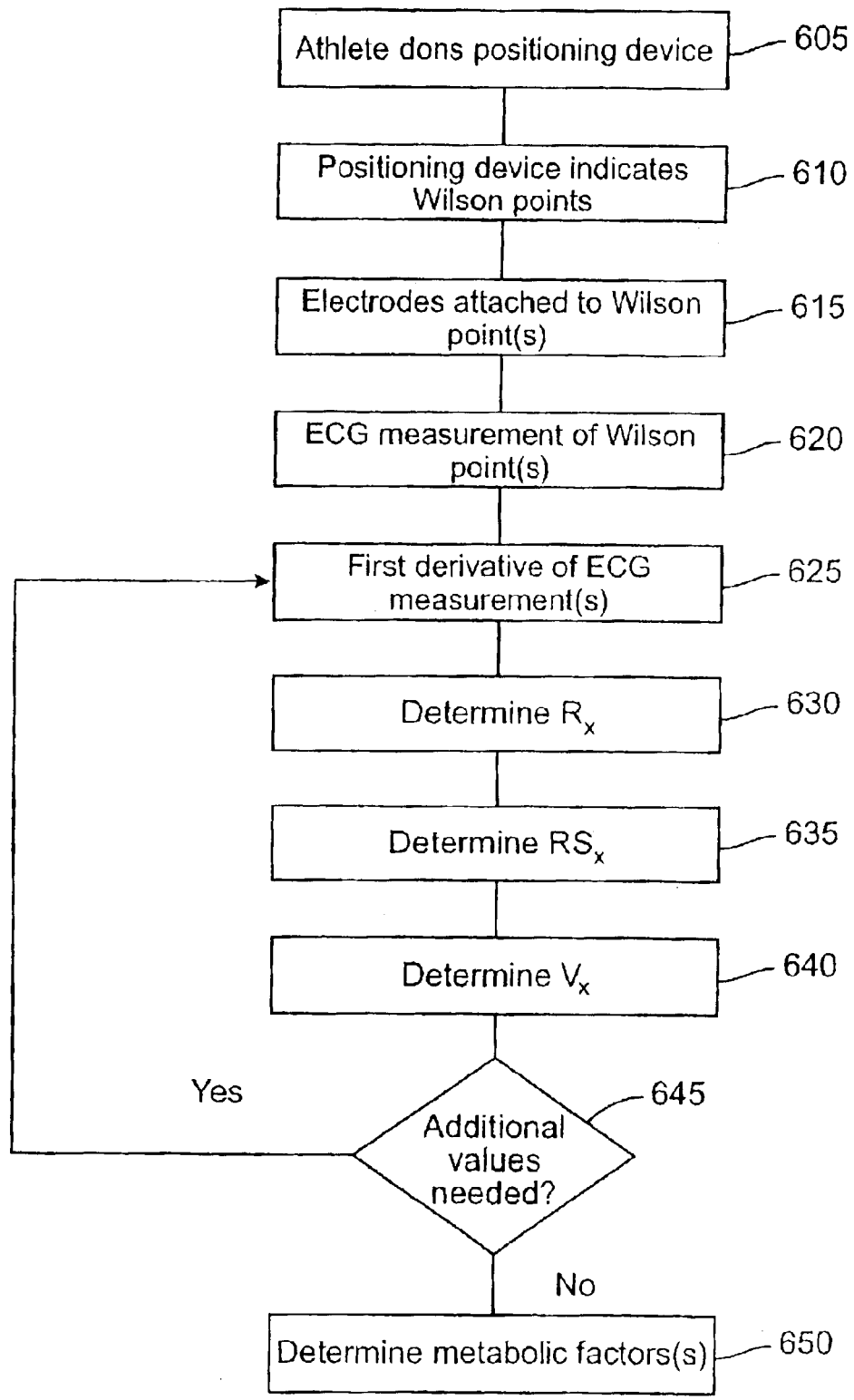
FIG. 6 is a flow chart which illustrates a method of determining a metabolic factor according to an embodiment of the present invention.

FIG. 5 illustrates a generalized process for determining secondary ECP factors (such as $W_{AnT}$, TMC and TAC), which require ECG measurements of more than one Wilson point. In step 505, an ECG signal is obtained from a Wilson point. The signal could be obtained, for example, via ECG 205, via a wireless link or over communications link 270. In step 510, the first derivative of the ECG signal is obtained. The first derivative could be calculated, for example by processor 285, or could be output from a circuit such as an operational amplifier. In step 515, $R_x$ is determined. In step 520, $RS_x$ is obtained. In step 525, $V_x$ (a number proportional to a primary ECP factor) is obtained by dividing $R_x$ by $RS_x$.

In step 530, a determination is made whether data are required from additional Wilson points in order to calculate the desired secondary ECP factor. This decision may be made, for example, by processor 285 based on software stored in memory 290. If additional data are required, the process returns to step 505, where another ECG signal is obtained. If sufficient data have been acquired, the process continues to step 635, wherein the secondary ECP factor is calculated.

Figure 9:
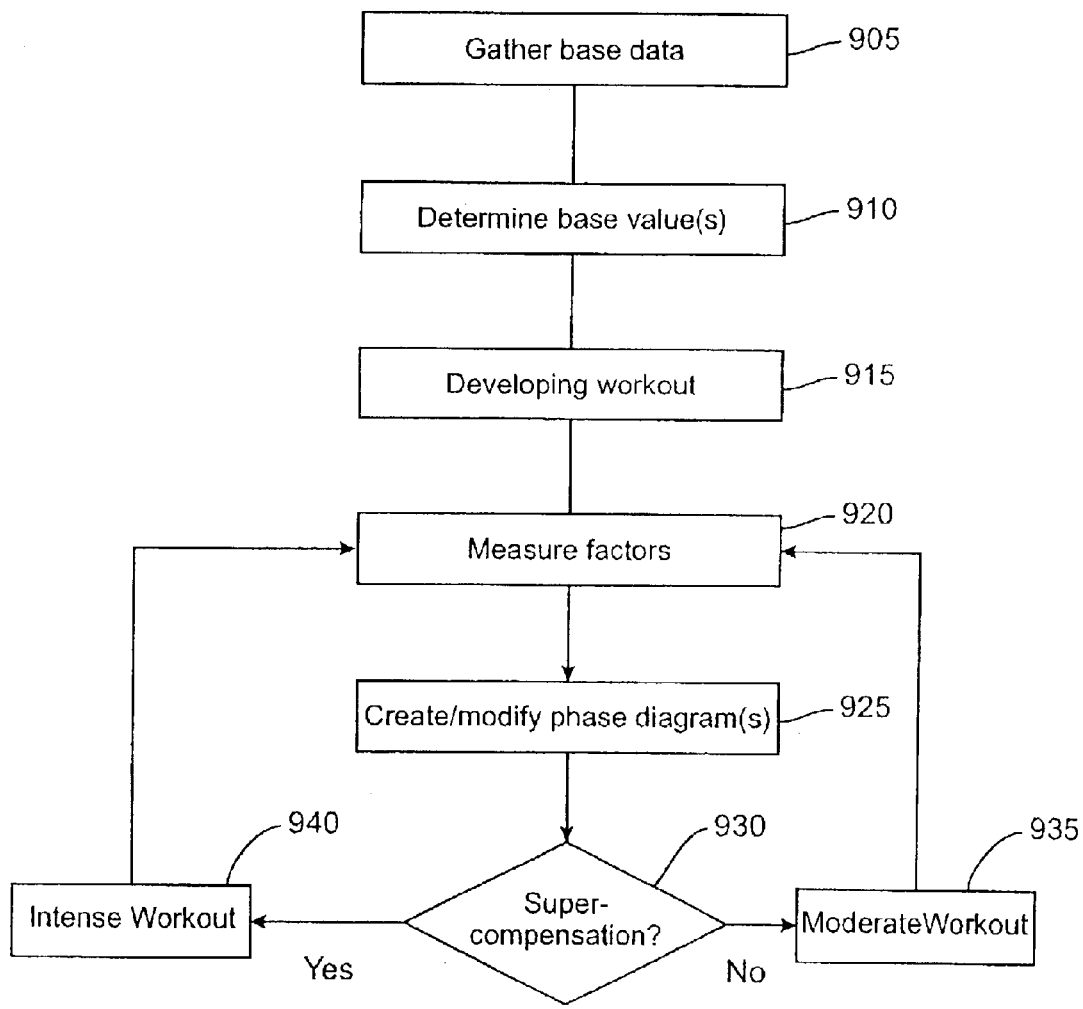
FIG. 9 is a flow chart which represents one method of designing an exercise program according to the present invention.

FIG. 9 is a flowchart which illustrates one method of combining the measurement of ECP factors with recommendations for appropriate workouts. In step 905, a person's ECP factors are measured at intervals over a period of time, e.g., 3 days. In step 910, the person's base values are calculated, typically by averaging the measured ECP factors. In some embodiments, such calculations are performed by processor 285, based on software stored in memory 290. In step 915, an appropriate developing workout is recommended and the person performs the workout. In step 920, the person's ECP factors are measured during the days following the developing workout. In step 925, data points of the ECP factors are plotted over time, creating phase diagrams for each ECP factor.

In step 930, a determination is made whether a person's ECP factor is in the supercompensation phase. This determination may be made, for example, 2 or 3 days after the developing workout and subsequent to a measurement of the person's ECP factors. If so, an intensive workout is recommended to the person. If not, a moderate workout is recommended. After the user performs the recommended workout, the ECP factors are measured again in step 920 and the phase diagrams are updated in step 925.

Devices for Facilitating the Measurement of Metabolic Factors

The methods and apparatus of the present invention are intended to be used by people of widely varying sophistication, from researchers and medical doctors on the one hand to lay persons on the other. Many people will find it difficult to locate reliably the V2, V3R and V6 Wilson points without some sort of assistance, either from another person, reference to a chart, etc. Accordingly, several devices are provided in order to facilitate the measurement of ECP factors by relatively unsophisticated people such as personal trainers, health club employees and end users.

Figure 10:
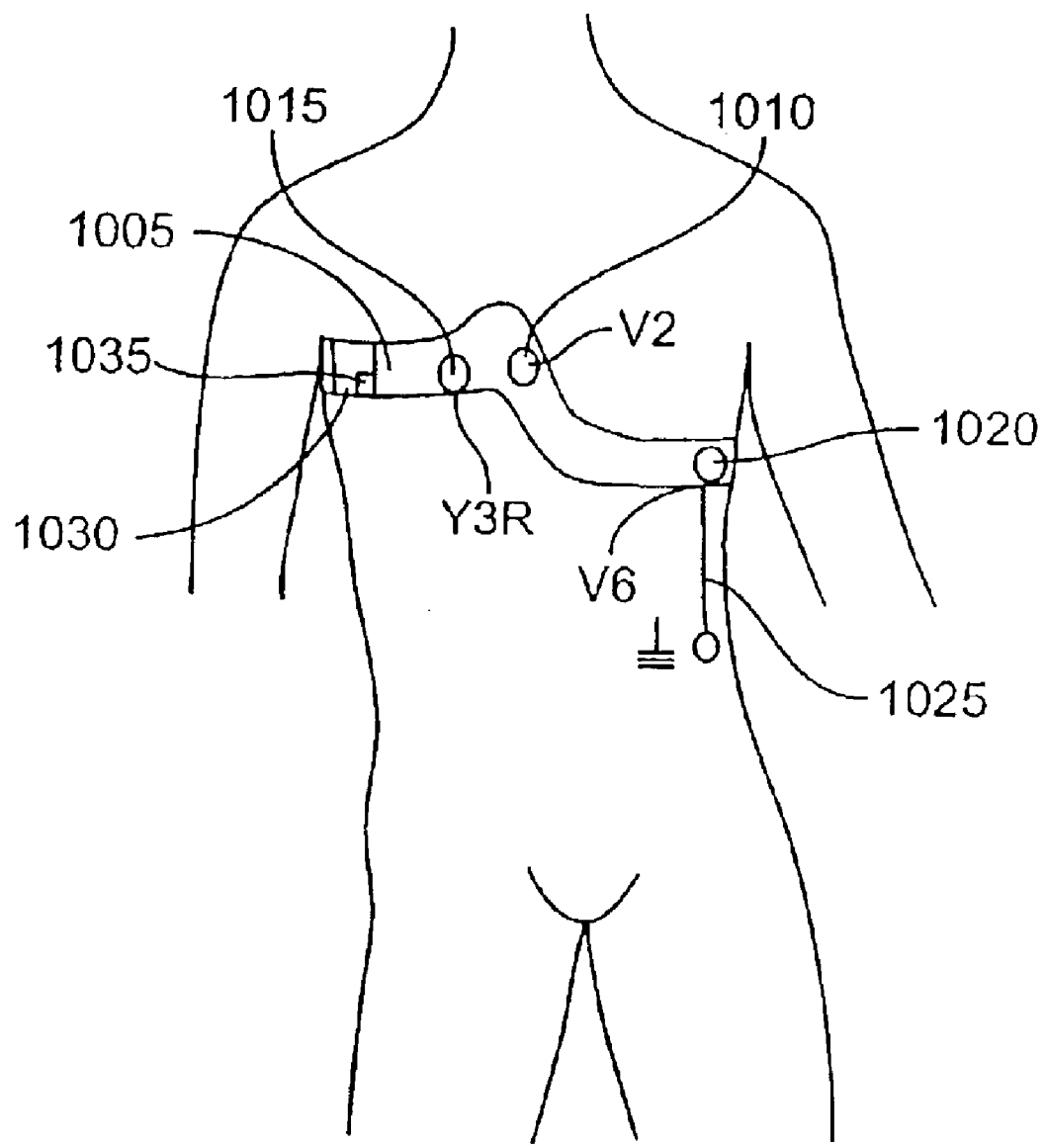
FIG. 10 is an illustration of a device which facilitates the measurement of ECG signals at one or more Wilson points.

FIG. 10 illustrates an embodiment of one such device. When worn as indicated in FIG. 10, passive electrocardiogram positioning garment 1005 conforms to the contours of a male person's chest, thereby aligning electrode positioning portions 1010, 1015 and 1020 with the person's V2, V3R and V6 Wilson points, respectively. In preferred embodiments, passive electrocardiogram positioning garment 1005 is at least partially made of elastic material, so that passive electrocardiogram positioning garment 1005 may accommodate a range of chest sizes. However, it is preferable that several sizes of passive electrocardiogram positioning garment 1005 are provided so that passive electrocardiogram positioning garment 1005 need not be stretched to more than about 5%–10% of its original circumference.

In some embodiments, electrode positioning portions 1010, 1015 and 1020 are openings for accommodating electrodes. In other embodiments, electrode positioning portions 1010, 1015 and 1020 are configured to attach an electrode to the wearer. In the embodiment shown in FIG. 10, passive electrocardiogram positioning garment 1005 includes input/output connection 1030, which allows electrode positioning portions 1010, 1015 and 1020 to be conveniently attached to another device for outputting ECG signals. In the embodiment shown in FIG. 10, passive electrocardiogram positioning garment 1005 also includes wireless transmitter 1035 for transmitting ECG signals from passive electrocardiogram positioning garment 1005 to another device, such as ECG 205. Alternative embodiments of passive electrocardiogram positioning garment 1005 include shoulder straps 1040 (not shown), which aid in reliably positioning passive electrocardiogram positioning garment 1005. Preferably, shoulder straps 1040 are adjustable.

Optional grounding device 1025 is normally omitted for embodiments in which electrode positioning portions 1010, 1015 and 1020 are openings for accommodating electrodes.

Figure 11:
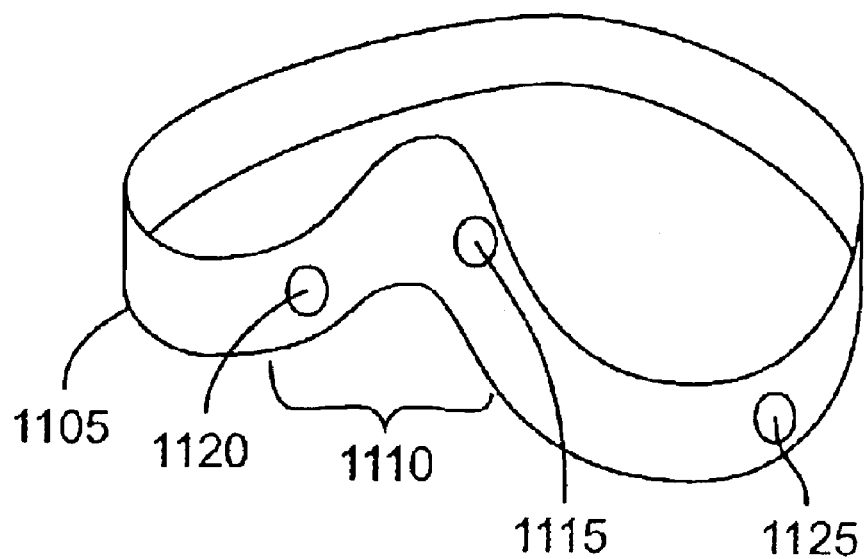
FIG. 11 is an embodiment of passive electrocardiogram positioning garment 1105 which is adapted for female users.

FIG. 11 is an embodiment of passive electrocardiogram positioning garment 1105 which is adapted for female users. Concave region 1110 is configured to accommodate the shape of a woman's right breast, thereby positioning electrode positioning portions 1015, 1020 and 1125 over the person's V2, V3R and V6 Wilson points, respectively. Alternative embodiments of passive electrocardiogram positioning garment 1105 include shoulder straps 1130 (not shown), which are similar in function to brassiere straps. Preferably, shoulder straps 1130 are adjustable. Some embodiments of passive electrocardiogram positioning garment 1105 are brassieres modified to include electrode positioning portions 1015, 1020 and 1125.

Figure 12:
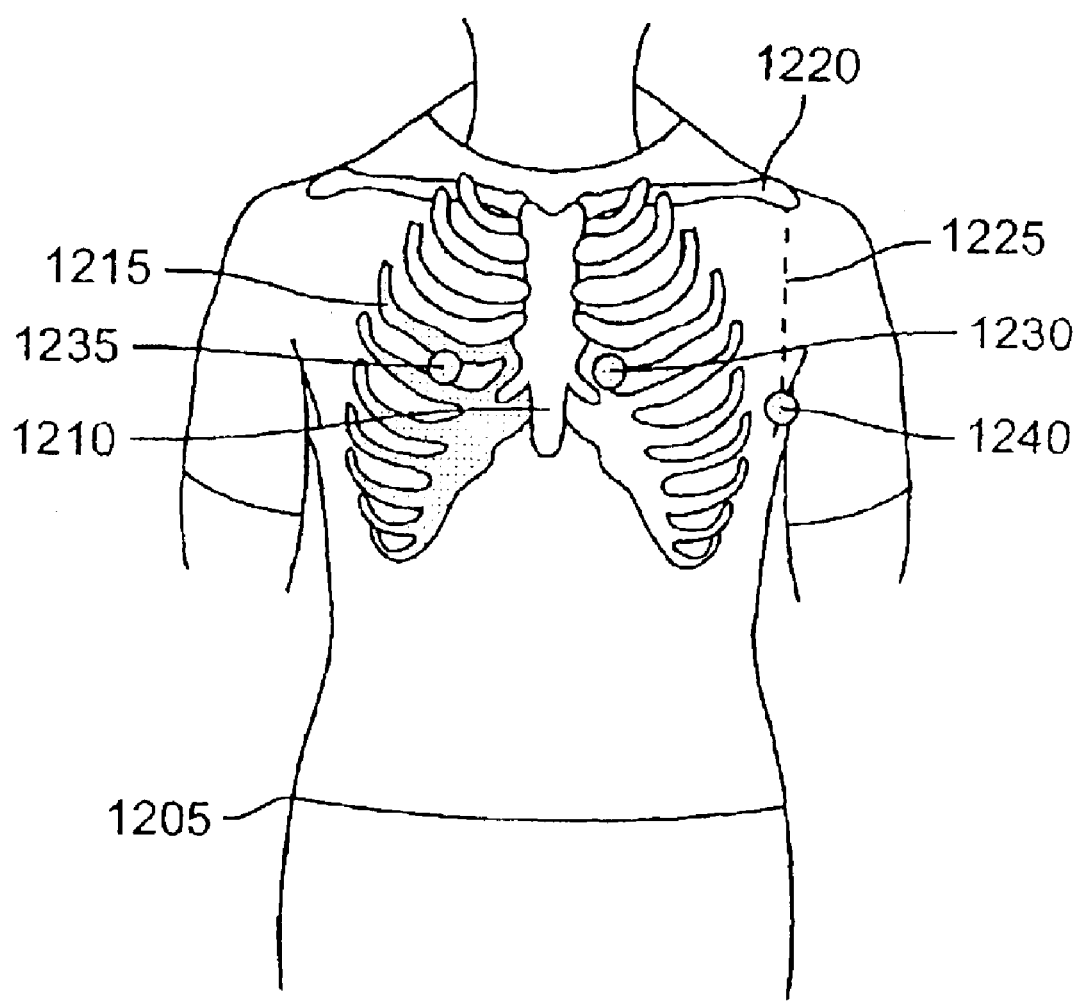
FIG. 12 is an embodiment of passive electrocardiogram positioning garment 1205, which includes an illustration of at least one of the anatomical references used to locate a Wilson point.

FIG. 12 is an embodiment of passive electrocardiogram positioning garment 1205, which includes an illustration of at least one of the anatomical references used to locate a Wilson point. Such anatomical references may include sternum 1210, one or more ribs 1215, clavicle 1220 and/or mid-axillary line 1225. If a user is wearing an appropriate size of passive electrocardiogram positioning garment 1205, the anatomical references should approximately conform to those of the wearer's body. Passive electrocardiogram positioning garment 1205 is preferably suspended from a user's shoulders and/or clavicle(s) (for sleeveless embodiments), for more reliably locating electrode positioning portions 1230, 1235 and 1240.

Monitoring Phases of ECP Factors and Designing an Exercise Schedule

The methods and devices for determining ECP factors according to the present invention facilitate the process of monitoring phases of these ECP factors. The following section describes methods and devices for monitoring phases of the ECP factors and interactively building an optimal exercise schedule. Various modifications of these embodiments (for example, those which vary the number of measurements, the time intervals between measurements. etc.) will be effective and are within the scope of the present invention.

1. Gathering Base Data.

On the first day ECP factors are measured every 3 hours, with a total of 5–6 measurements for the day. In preferred embodiments, at least La, PhC, and $VO_2$ Max are measured. The first measurement should be taken immediately after waking up. On the second and third days, 3 measurements are taken—one in the morning, one at midday and one in the evening. In some alternative embodiments, base data are gathered for 1 or 2 days instead of 3. However, such alternative embodiments do not establish base values as reliably as methods which use a 3-day period to gather base data. In other embodiments, base data are gathered for more than 3 days.

Although the ECP factors may be recorded in any convenient fashion (e.g., by writing them on paper), in preferred embodiments the ECP factors are stored in a memory. In many embodiments, the ECP factors are stored in one of the memory devices of ECG 205 and/or computer 210.

2. Calculating Base Values.

The base values are determined by the various ECP factors which are measured in step 1. In some embodiments, the base values are simply the average values of the ECP factors. In other embodiments, the base values are the mean, the median, or are weighted to account for factors such as the time of day, activity of the person measured, etc. In preferred embodiments, the ECP factors are stored in a memory (such as memory 290) and the base values are determined by a processor (such as processor 285) which executes software to calculate the base values.

3. Developing Workout.

A developing workout for all three energy conversion processes should be performed after the base values are determined. In this embodiment, the developing workout takes place on the 4th day and is structured as follows: (1) a warm-up (approximately 15 min.); (2) intensive anaerobic-alactic exercises (approximately 15 min.); (3) intensive anaerobic-lactic exercises (approximately 20–25 min.); and (4) intensive aerobic exercises (approximately 40–45 min.).

The time intervals indicated for the developing workout are merely examples. The intensity and duration of the workout should correspond with the physical condition of the person who is working out. Similarly, the types of exercises should be determined to fit the athletic orientation of the person who is working out.

For example, a person who is primarily interested in running and is already in good physical condition could have a developing workout similar to the following: (1) a 10 to 15 minute warm-up (e.g., of stretching out); (2) short (e.g., 8–10 second) maximal intensity sprints from a resting position, followed by periods of complete restitution, for a total time of 20 minutes; (3) jogging, then accelerating to a maximum speed for 1 or 2 minutes, then jogging during a partial restitution phase, then accelerating to a maximum speed for 1 or 2 minutes, for a total time of up to 20 minutes; and (4) running for 20–30 minutes while keeping the heart rate near the $HR_{AnT}$ value.

In some embodiments, various possible workouts are stored in a memory (such as memory 290). Recommended workouts are suggested to a user based on the user's base ECP factor values, on input received from the user or on other data.

4. Measuring ECP Factors After the Developing Workout.

ECP factors should be measured after the developing workout. In one embodiment, the ECP factors are measured 10 minutes, 1 hour, 3 hours, and 24 hours after the developing workout. In other embodiments, the ECP factors are measured again after a longer time, e.g. 36 and 48 hours after the developing workout. In some embodiments, the ECP factors are measured more often during the first few hours after the developing workout, or otherwise measured at different time intervals.

5. Determining the Phases of the ECP Factors

It is important to determine the phases of each ECP factor, especially the supercompensation phase, in order to allow a user to work out or compete at the optimum times. The present invention encompasses various methods of determining these phases and of providing information regarding the phases and corresponding recommended workouts.

In some embodiments, a display is prepared which indicates the values for each ECP factor at different time intervals. Such a display could be provided on display 225, by a separate display of computer 210, on a device in communication with computer 210 and/or ECG 205, in hard copy form or in any other convenient fashion.

In one such embodiment the display is a graphical display (a "phase diagram"), with time plotted on the x axis and the ECP factor value plotted on the y axis. The value may be displayed in any convenient fashion, e.g., in absolute terms, as a percentage of its base value, etc. In one such embodiment, the zero position on the y axis corresponds to 100% of the base value of the ECP factor. The values of the ECP factors measured after the developing workout are plotted on the graph. The values of the ECP factors may be plotted manually, but in preferred embodiments the values are stored in memory and plotted by a computer. In some such embodiments, the phases of each ECP factor are input to a memory and a processor computes a curve which best fits the changing values of the ECP factors over time.

However, in some embodiments, no graphical display is created. In some such embodiments, the times for the supercompensation phase of each factor are reported to a user, but not in graphical form. In some embodiments, the user is notified via e-mail. In other embodiments, the user is notified via pager. In yet other embodiments, the user is notified by telephone. In some such embodiments, the user is notified via communications link 270.

6. Timing and Intensity of Subsequent Workouts Based upon the Phases of the ECP Factors ECP factors should be measured and recorded before exercising. The ECP factors should be compared with the base values, e.g., by plotting the newly recorded values on a phase diagram. In preferred embodiments, the ECP factors are stored in a memory and a processor executes a program for comparing a most recent ECP factor with a base value and/or past ECP factors.

When an ECP factor reaches the supercompensation phase (zone 3 of FIG. 8), an intensive workout should be performed for the corresponding energy conversion system. Otherwise, a moderate restitution workout should be performed, without putting too much strain on any of the energy conversion systems. As a rough guideline, if a person is in reasonably good physical condition, an ECP factor should be in the range of 20% to 25% above its base value during the supercompensation phase. Therefore, according to one embodiment of the present invention, at or near a time when a person's ECP factors reach a predetermined level in excess of the corresponding base value (e.g., a level exceeding 20% of the base value), the person is notified that he or she should perform a developing workout.

If a person has not exercised regularly prior to beginning of an exercise program using the methods of the present invention, the differences between phases of the ECP factors may not be very significant. In such cases, the values of ECP factors during a supercompensation phase may not exceed 20% of the base value. The supercompensation phase can still be determined, however, by measuring the ECP factors and determining when these factors reach a maximum. According to some embodiments of the present invention, a person is notified that he or she should engage in a developing workout at or near a time when the corresponding ECP factor reaches a maximum value, regardless of the absolute value of the ECP factor or its increase relative to the base value. In some such embodiments, a processor in ECG 205 or computer 210 (for example, processor 285) determines when the maximum value has been determined. In some embodiments, the values are plotted on a display, such as a phase diagram, and a person determines by inspection when a maximum value has been attained. In other embodiments, the person is notified by pager, facsimile, e-mail, telephone or printout, or via a display of ECG 205, of computer 210 or of a networked device.

Phases of energy conversion processes are cyclical, so once enough measurements are accumulated it becomes possible to make a prognosis of the phases of ECP factors which will occur in the future. The time interval between a developing workout and a supercompensation period will vary to some degree, but once the interval has been measured it can provide an estimate as to the length of time until the next interval. According to some embodiments of the present invention, a person engages in a developing workout at or near a time when the corresponding ECP factor should be reaching a maximum value, based on previous measurements of the interval between prior developing workouts and prior supercompensation periods. In some embodiments, a processor in ECG 205 or computer 210 determines when a supercompensation phase should be occurring. In some such embodiments, the person is electronically notified (e.g., by pager, facsimile, telephone or e-mail) when the corresponding ECP factor should be reaching a maximum value. In some such embodiments, the notification takes place via communications link 270.

7. Recalibrating Base Values

The base values should be recalculated after a period of time. In one embodiment, the base values are recalibrated every two months. After recalculating the base value, a developing workout should normally be performed.

Base values may be recalibrated using at least two general methods, with many possible variations of each method. According to one general method, the base values are recalibrated by ceasing the exercise program for several days, then repeating steps 1 and 2, above. Various embodiments of this method involve ceasing the exercise program for varying lengths of time, measuring ECP factors at different intervals, measuring ECP factors for different lengths of time, taking different total numbers of ECP measurements, etc.

According to alternative methods, the base values are recalibrated without ceasing the exercise program. According to some such embodiments, base values are recalibrated by taking the average of recent ECP measurements. These embodiments differ primarily in the number of measurements and/or the time period used in the averaging process. According to other embodiments, base values are recalibrated by reference to the minimum (decompensation) and maximum (supercompensation) phases. In some such embodiments, base values are recalibrated by taking an average of the maximum and minimum values for recent cycles of decompensation and supercompensation. In other embodiments, the recalibration includes a biasing factor which accounts for historical variations from the base values.

Sample Workouts Based on Phases of ECP Factors

Specific exercises and the level of physical load of each episode of an athletic training program depend on both the current phase of ECP factors and their values measured immediately before the episode.

The duration and intensity of athletic exercises are proportional to the values of ECP factors. The preferred method of monitoring the quality of a workout is by determining the difference between values of ECP factors taken before and 20–30 minutes after exercise. Exercises of optimal duration and intensity should deplete ECP factors up to 40–45%. The less the level of depletion is, the less the following supercompensation amplitude will be, making the training episode less efficient. However, for someone who has not recently exercised a great deal, it may be advisable to start out with lower levels of depletion.

The devices and methods of the present invention are applicable to any specific type of athletic exercise. A coach or trainer will be able to determine types of exercises for professional athletes or other competitive athletes. Amateur athletes and people who engage in physical training for recreational or health purposes can be very flexible in choosing individual training programs.

The following paragraphs set forth specific exercises for different phases of ECP factors. A person first measures the ECP factors, then determines which category of exercises is most appropriate to the current ECP factor values. These exercises may be modified as appropriate to each person's goals, athletic condition and related factors. As noted above, in some embodiments of the present invention, sample workouts are stored in a memory (such as memory 290) and are correlated with a measured phase of one or more ECP factors, as noted below. A recommended workout is communicated to the user according to a measured or estimated phase of the ECP factors.

If all ECP factors are at their base levels or 5–10% below, a person should engage in a stimulating (restitution) workout. Types of exercises appropriate for a restitution workout include stretching, push-ups, chin-ups, moderate intensity swimming, running or bicycling with heart rate in the AeT–AnT range. If a person is involved in team sports, a workout which focuses on technique or tactics would be appropriate. The recommended duration varies according to the person's level of conditioning, but is typically 1 hour or less.

If the ECP factors remain at or near the same level for more than one episode of training, the developing workout should be repeated. The developing workout should concentrate on specific muscular activity, defined as activity that makes use of the muscle groups specific for the athletic orientation of a professional athlete or the most typical activity of an amateur or recreational athlete. For example, a cyclist should focus on cycling, on development of the muscles used when cycling, etc.

If the anaerobic-alactic energy conversion factor is in the supercompensation phase, the person should perform short (8–15 second) spurts of the most intensive load with complete restitution (heart rate 5–15% below the AeT level.) The number of repetitions should typically be in the range of 8–15. However, this number depends on the amplitude of the supercompensation phase of the anaerobic-alactic ECP factor, which should increase as the person's athletic performance increases.

If the anaerobic-lactic energy conversion factor is in the supercompensation phase, the workout should include medium (20 second–4 min) spurts of the most intensive load with incomplete restitution. The heart rate should not drop lower than about 5% below AeT level, even between repetitions. For a well-trained athlete the heart rate should not drop below the AeT level. The number of reps should typically be in the range of 5–10, based on the value of the La ECP factor. The activity can be either specific or non-specific, since the main goal of the training is create larger reserves of glycogen in the future (upon the onset of a supercompensation phase) by depleting them during this episode of training.

If the aerobic energy conversion factor is in the supercompensation phase, the workout should include submaximal repetitive activity, such as running; swimming, bicycling, etc. In preferred embodiments, the heart rate is constantly monitored in order to maintain the heart rate at approximately the AnT level. The duration of a workout should generally be in the range of 45–70 minutes, but should vary based on the person's level of aerobic conditioning. Before the workout, a 10–15 minute warm-up is preferred.

If both anaerobic (lactic and alactic) energy conversion factors are in the supercompensation phase, the workout should include spurts of maximal intensity with incomplete restitution. The duration of each spurt should generally be in the range of 40–200 seconds. For a beginner, with a relatively small increase in amplitude during the supercompensation phase, the number of repetitions should be in the range of 5–8.

If both the aerobic and either of the anaerobic energy conversion factors are in the supercompensation phase, the workout should include a specific anaerobic workout, as described above. An additional 20–30 minutes of repetitive aerobic activity with the heart rate near the AnT level should also be performed.

If all ECP factors are more than 10% below their base values, the person should rest. The person should either skip the day or measure the ECP factors again later that day, e.g., in 5–6 hours.

As a person proceeds with an exercise schedule according to the present invention, the differences between values of ECP factors during different phases should become more and more noticeable. Moreover, the phases of all energy conversion systems will tend to converge, and each super-compensation phase will be greater in amplitude.

Combining the prognosis method with altering the exercise schedule becomes a powerful tool in maximizing athletic performance, whether used in preparing for athletic competitions or for optimizing the results of a non-competitive exercise routine.

While the best mode for practicing the invention has been described in detail, those of skill in the art will recognize that there are numerous alternative designs, embodiments, modifications and applied examples which are within the scope of the present invention. Accordingly, the scope of this invention is not limited to the previously described embodiments.

We claim:

1. A non-invasive method for determining a metabolic factor, comprising the steps of:
   obtaining a first derivative of an electrocardiogram measurement;
   determining $R_x$, an absolute value of a positive spike of the first derivative;
   determining $RS_x$, a sum of absolute values of the positive and negative spikes of the first derivative; and
   dividing $R_x$ by $RS_x$ to determine $V_x$, a number proportional to the metabolic factor.

2. The method of claim 1, further comprising the step of multiplying $V_x$ by a constant to determine the metabolic factor.

3. The method of claim 2, wherein:
   the electrocardiogram measurement is taken from the V6 Wilson point;
   the metabolic factor is aerobic capacity; and
   the constant is approximately 120.

4. The method of claim 2, wherein:
   the electrocardiogram measurement is taken from the V2 Wilson point;
   the metabolic factor is lactacidemia; and
   the constant is approximately 30.

5. The method of claim 2, wherein:
   the electrocardiogram measurement is taken from the V3R Wilson point;
   the metabolic factor is phosphocreatine capacity; and
   the constant is approximately 115.

6. An apparatus for determining metabolic factors from electrocardiogram measurements, comprising:
   means for obtaining a first derivative of an electrocardiogram measurement;
   means for determining $R_x$, an absolute value of a positive spike of the first derivative;
   means for determining $RS_x$, a sum of absolute values of the positive and negative spikes of the first derivative; and
   means for dividing $R_x$ by $RS_x$ to determine $V_x$, a number proportional to the metabolic factor.

7. The apparatus of claim 6, further comprising means for multiplying $V_x$ by a constant to determine the metabolic factor.

8. The apparatus of claim 6, wherein the means for obtaining the first derivative comprises a processor.

9. The apparatus of claim 6, wherein the means for obtaining the first derivative comprises a circuit to which an electrocardiogram measurement is input and which outputs the first derivative of the electrocardiogram measurement.

10. The apparatus of claim 6, further comprising means for converting analog signals from the electrocardiogram unit into digital form.

11. The apparatus of claim 6, further comprising display means.

12. The apparatus of claim 6, further comprising communication means for communicating with one or more devices.

13. The apparatus of claim 7, wherein:
    the electrocardiogram measurement is taken from the V6 Wilson point;
    the metabolic factor is aerobic capacity; and
    the constant is approximately 120.

14. The apparatus of claim 7, wherein:
    the electrocardiogram measurement is taken from the V2 Wilson point;
    the metabolic factor is lactacidemia; and
    the constant is approximately 30.

15. The apparatus of claim 7, wherein:
    the electrocardiogram measurement is taken from the V3R Wilson point;
    the metabolic factor is phosphocreatine capacity; and
    the constant is approximately 115.

16. An apparatus for determining metabolic factors from electrocardiogram measurements, comprising:
    an input for receiving signals from an electrocardiogram unit;
    a processor for executing one or more software programs to determine $R_2$, $R_6$, $RS_2$ and $RS_6$, for calculating $V_2$ and $V_6$, and for performing an operation on $V_2$ and $V_6$ to determine the metabolic factor; and
    a memory for storing the software programs, wherein:
    $R_2$ is an absolute value of a positive spike of a first derivative of an electrocardiogram measurement of a V2 Wilson point;
    $RS_2$ is a sum of absolute values of the positive and negative spikes of the first derivative of the electrocardiogram measurement of the V2 Wilson point;
    $R_6$ is an absolute value of the positive spike of a first derivative of an electrocardiogram measurement of a V6 Wilson point;
    $RS_6$ is the sum of absolute values of the positive and negative spikes of the first derivative of the electrocardiogram measurement of the V6 Wilson point;
    $V_2$ equals $R_2$ divided by $RS_2$; and
    $V_6$ equals $R_6$ divided by $RS_6$.

17. The apparatus of claim 16, further comprising an analog-to-digital unit for converting analog signals from the electrocardiogram unit into digital form.

18. The apparatus of claim 16, further comprising a display unit.

19. The apparatus of claim 16, wherein:
    the metabolic factor is metabolic power at an anaerobic threshold ($W_{AnT}$); and
    the operation comprises dividing $V_6$ by the sum of $V_6$ and $V_2$.

20. The apparatus of claim 19, wherein the processor also determines a heart rate at an anaerobic threshold and wherein the operation further comprises adding $W_{AnT}$, $V_6$ and $V_2$.

21. The apparatus of claim 19, wherein the processor also determines a heart rate at an aerobic threshold and wherein the operation comprises:
    multiplying $W_{AnT}$ and $V_6$;
    dividing the result of the multiplying step by 100; and
    adding $V_2$ and $W_{AnT}$ to the result of the dividing step.

* * * * *